United States Patent [19]

Brenner et al.

[11] 4,001,426
[45] Jan. 4, 1977

[54] SUBSTITUTED BENZOFURANS AND BENZOTHIOPHENES

[75] Inventors: L. Martin Brenner, Havertown; Charles K. Brush, Malvern, both of Pa.

[73] Assignee: SmithKline Corporation, Philadelphia, Pa.

[22] Filed: May 9, 1975

[21] Appl. No.: 575,877

Related U.S. Application Data

[63] Continuation-in-part of Ser. No. 515,808, Oct. 17, 1974, abandoned, which is a continuation-in-part of Ser. No. 462,008, April 18, 1974, abandoned.

[52] U.S. Cl. .................. 424/285; 260/247.1 P; 260/247.7 T; 260/268 BC; 260/293.57; 260/293.58; 260/326.5 SA; 260/326.5 C; 260/330.5; 260/346.2 R; 424/248.51; 424/250; 424/267; 424/274; 424/275; 424/248.56; 424/248.58
[51] Int. Cl.² .................................... C07D 405/12
[58] Field of Search ............ 260/247.1 P, 247.7 G, 260/268 BC, 293.57, 293.58, 326.5 SA, 326.5 C, 330.5, 346.2 R; 424/248, 250, 267, 274, 275, 285

[56] References Cited

UNITED STATES PATENTS

| 3,147,280 | 9/1964 | Jurd ........................ 260/343.2 |
| 3,248,401 | 4/1966 | Tondeur et al. ............ 260/346.2 |
| 3,394,125 | 7/1968 | Crenshaw .................. 260/326.5 |
| 3,880,891 | 4/1975 | Hill et al. .................. 260/346.2 R |

Primary Examiner—G. Thomas Todd
Attorney, Agent, or Firm—Janice E. Williams; William H. Edgerton; Alan D. Lourie

[57] ABSTRACT

The compounds are benzoyl benzofurans and benzothiophenes having pharmacological activity, in particular, coronary vasodilator activity useful for the treatment of angina pectoris and intermediates for the preparation thereof.

23 Claims, No Drawings

SUBSTITUTED BENZOFURANS AND BENZOTHIOPHENES

This application is a continuation-in-part of Ser. No. 515,808, filed Oct. 17, 1974, now abandoned, which is a continuation-in-part of Ser. No. 462,008, filed Apr. 18, 1974, now abandoned.

This invention relates to new benzoyl benzofurans and benzothiophenes which have useful pharmacological activity. More specifically, these compounds have coronary vasodilator activity and are useful in the treatment of angina pectoris. In addition, these compounds may be useful as hypotensive agents. Also included in this invention are intermediates for the preparation of the benzoyl benzofurans and benzothiophenes.

The benzoyl benzofurans and benzothiophenes of this invention are represented by the following structural formula:

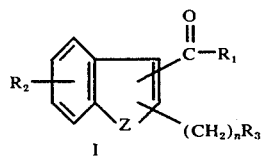
I or pharmaceutically acceptable acid addition salt thereof, in which:

$R_1$ is phenyl, halophenyl, dihalophenyl, trihalophenyl, lower alkylphenyl, di-lower alkylphenyl, tri-lower alkylphenyl, lower alkoxyphenyl, di-lower alkoxyphenyl, tri-lower alkoxyphenyl, lower alkyl-di-lower alkoxyphenyl or lower alkoxy-di-lower alkylphenyl;

$R_2$ is hydrogen, halo, lower alkyl, lower alkoxy, nitro or trifluoromethyl;

$R_3$ is 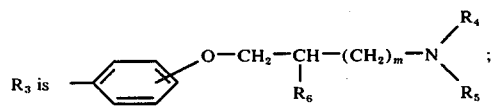 ;

$R_4$ is hydrogen, methyl, ethyl or propyl and $R_5$ is methyl, ethyl or propyl or $R_4$ and $R_5$ together with the nitrogen atom to which they are attached form a pyrrolidine, piperidine, N-(lower alkyl)piperazine, morpholine or perhydroazepine ring;

$R_6$ is hydrogen or hydroxy;

m is 0 or 1 when $R_6$ is hydrogen and 1 when $R_6$ is hydroxy;

n is 0 or 1; and

Z is oxygen or sulfur.

As used herein, the terms "lower alkyl" and "lower alkoxy" denote groups having from one to four carbon atoms; "halo" refers to fluoro, chloro and bromo.

Advantageous compounds of this invention are represented by formula I in which $R_4$ is hydrogen, methyl, ethyl or propyl; $R_5$ is methyl, ethyl or propyl; $R_1$, $R_2$, $R_3$, $R_6$, m and n are defined as above and Z is oxygen.

Most advantageous are the compounds of formula I in which

is in the 3-position of the heterocyclic nucleus; $R_1$ is dihalophenyl, trihalophenyl, di-lower alkylphenyl, tri-lower alkylphenyl, di-lower alkoxyphenyl, tri-lower alkoxyphenyl, lower alkyl-di-lower alkoxyphenyl or lower alkoxy-di-lower alkylphenyl; $R_2$ is hydrogen, halo or lower alkyl; —$(CH_2)_nR_3$ is in the 2-position of the heterocyclic nucleus; $R_3$ is

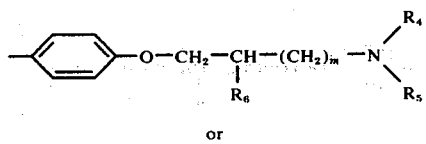

or

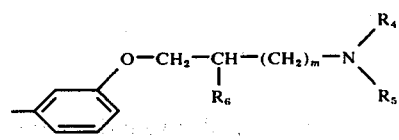

$R_4$ and $R_5$ are methyl, ethyl, propyl or together with the nitrogen atom to which they are attached form a pyrrolidine, piperidine, N-(lower alkyl)piperazine, morpholine or perhydroazepine ring; $R_6$ is hydrogen; m and n are 0 or 1 and Z is oxygen.

Preferred compounds of this invention are represented by formula I in which

is in the 3-position of the heterocyclic nucleus; $R_1$ is halophenyl, 3,5-dihalophenyl, 3,5-di-lower alkylphenyl, 3,4,5-tri-lower alkylphenyl, 3,5-di-lower alkoxyphenyl or 3,5-di-lower alkyl-4-lower alkoxyphenyl; $R_2$ is hydrogen or halo; —$(CH_2)_nR_3$ is in the 2-position of the heterocyclic nucleus; $R_3$ is

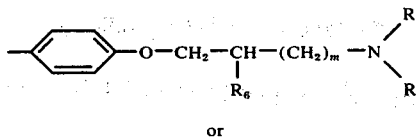

or

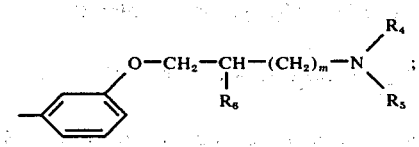

$R_4$ and $R_5$ are methyl, ethyl, propyl or together with the nitrogen atom to which they are attached form a pyrrolidine, piperidine, N-(lower alkyl)piperazine, morpholine or perhydroazepine ring; $R_6$ is hydrogen; m and n are 0 or 1 and Z is oxygen.

Most preferred compounds are represented by formula I in which

is in the 3-position of the heterocyclic nucleus; $R_1$ is chlorophenyl, 3,5-dimethylphenyl, 3,4,5-trimethylphenyl, 3,5-dimethoxyphenyl or 3,5dimethyl-4-methoxyphenyl; $R_2$ is hydrogen or chloro; —$(CH_2)_nR_3$ is in the 2-position of the heterocyclic nucleus; n is 0; $R_3$ is

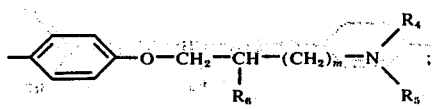

$R_4$ and $R_5$ are ethyl or together with the nitrogen atom to which they are attached form a pyrrolidine or piperidine ring; $R_6$ is hydrogen; m is 0 and Z is oxygen.

Especially preferred are the compounds of formula I in which

is in the 3-position of the heterocyclic nucleus; $R_1$ is chlorophenyl, 3,5-dimethylphenyl, 3,4,5-trimethylphenyl, 3,5-dimethoxyphenyl or 3,5-dimethyl-4-methoxyphenyl; $R_2$ is hydrogen or chloro; —$(CH_2)_nR_3$ is in the 2-position of the heterocyclic nucleus; n is 0; $R_3$ is

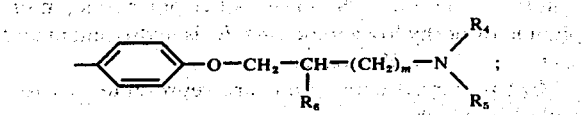

$R_4$ and $R_5$ are ethyl; $R_6$ hydrogen; m is 0 and Z is oxygen.

Particularly preferred are those compounds of this invention which, in addition to having coronary vasodilator activity, also inhibit or attenuate the chronotropic effect of isoproterenol-induced tachycardia, for example 2-[4'-(2-diethylaminoethoxy)phenyl]-3-(3',5'-dimethylbenzoyl)benzofuran, 2-]4'-(2-diethylaminoethoxy)phenyl]-3-(3', 4', 5'-trimethyl-benzoyl)benzofuran, 5-chloro-2-[4'-(2-diethylaminoethoxy)-phenyl]-3-(3',5'-dimethylbenzoyl)benzofuran, 3-(3', 5'-dimethyl-benzoyl)-2-[4'-(2-N-pyrrolidinoethoxy)phenyl]benzofuran, 3-(3',5'-dimethylbenzoyl)-2-[4'-(2-N-piperidinoethoxy)phenyl]-benzofuran and 2-(4'-chlorobenzoyl)-3-[4'-(2-hydroxy-3-isopropylaminopropoxy)phenyl]benzofuran.

Preferred benzothiophene compounds are 2-[4'-(2-diethylaminoethoxy)phenyl]-3-(3',5'-dimethylbenzoyl)benzothiophene, 5-chloro-2-[4'-(2-diethylaminoethoxy)phenyl]-3-(3',5'-dimethylbenzoyl)benzothiophene and 3-[4'-(2-diethylaminoethoxy)phenyl]-2-(3',5'-dimethylbenzoyl)benzothiophene.

Some of the compounds of this invention may exist as optical isomers due to an asymmetric carbon atom in the aminoalkoxy side chain. All of the isomers, including separated isomers and mixtures thereof, are included within the scope of this invention.

The compounds of formula I in which

is in the 3-position, —$(CH_2)_nR_3$ is in the 2-position and $R_6$ is hydrogen are prepared as shown in the following scheme:

SCHEME 1

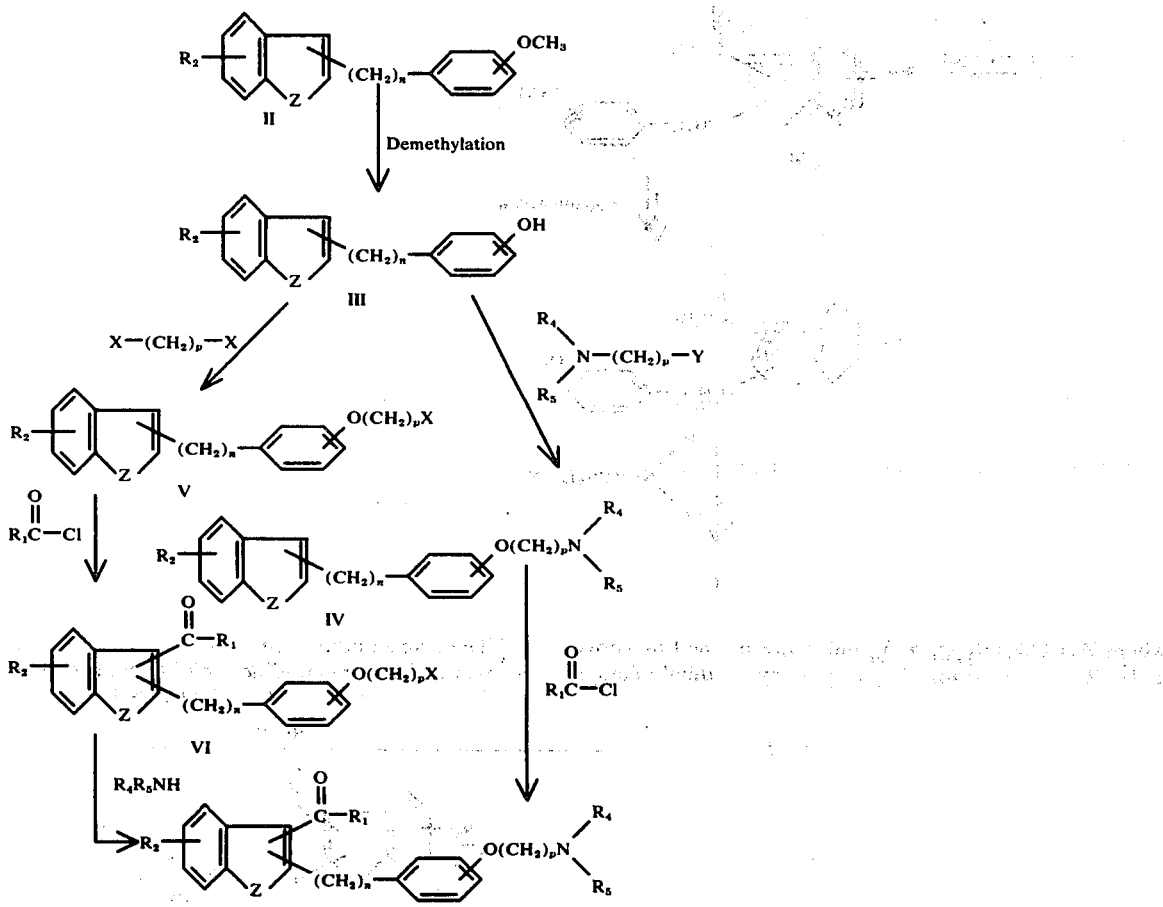

in which the terms $R_1$, $R_2$, $R_4$, $R_5$, n and Z are defined as above, p is 2 or 3, X is halo, preferably chloro or bromo and Y is halo, preferably chloro, or a leaving group such as tosyl or mesyl.

According to the above procedure, a methoxyphenyl or methoxybenzyl benzofuran or benzothiophene of formula II is demethylated by known methods, for example by use of pyridine hydrochloride or boron tribromide, to the corresponding hydroxyphenyl or hydroxybenzyl benzofuran or benzothiophene of formula III. Reaction of III with a substituted aminoalkyl halide or tosylate of the formula $R_4R_5N-(CH_2)_p-Y$ in the presence of a base such as potassium carbonate, sodium methoxide or sodium hydride in a solvent such as acetone, methanol, toluene, 3-pentanone or dimethylsulfoxide followed by acylation of the product aminoalkoxyphenyl or aminoalkoxybenzyl benzofuran or benzothiophene (IV) or the corresponding salt, preferably a hydrochloride salt, with an acid chloride of the formula $$R_1\overset{\overset{O}{\|}}{C}-Cl$$

by standard procedures, for example in the presence of stannic chloride or aluminum chloride in a solvent such as methylene chloride, nitrobenzene or carbon disulfide at a temperature from about 0° C. to ambient temperature (ca. 25° C.) gives compounds of formula I where $R_6$ is hydrogen.

These benzoyl benzofurans and benzothiophenes are also prepared as shown in Scheme 1 from the intermediate of formula III by reaction of III with a dihaloalkane, $X-(CH_2)_p-X$, preferably dibromo or dichloro, in the presence of a base such as potassium carbonate in a solvent such as acetone or 3-pentanone, preferably at the reflux temperature, followed by acylation as previously described of the haloalkoxyphenyl or haloalkoxybenzyl benzofuran or benzothiophene (V) thus formed to give a haloalkoxyphenyl- or benzyl-3-benzoyl benzofuran or benzothiophene (VI). Treatment of VI with an amine of the formula $R_4R_5NH$ where $R_4$ and $R_5$ are defined as above in a solvent such as refluxing ethanol, gives the corresponding compounds of formula I.

Also included within this invention are the compounds of formula IV shown in Scheme 1. In addition to being useful as intermediates in the preparation of compounds of formula I, these aminoalkoxyphenyl and benzyl benzofurans and benzothiophenes, such as the compound where the side chain is in the 2-position of the nucleus, $R_2$ is hydrogen, $R_4$ and $R_5$ are ethyl, n is 0, p is 2 and Z is oxygen, also have coronary vasodilator activity.

In addition, when $R_1$ does not contain an alkoxy group(s), the corresponding compounds of formula I are prepared as shown below:

SCHEME 2

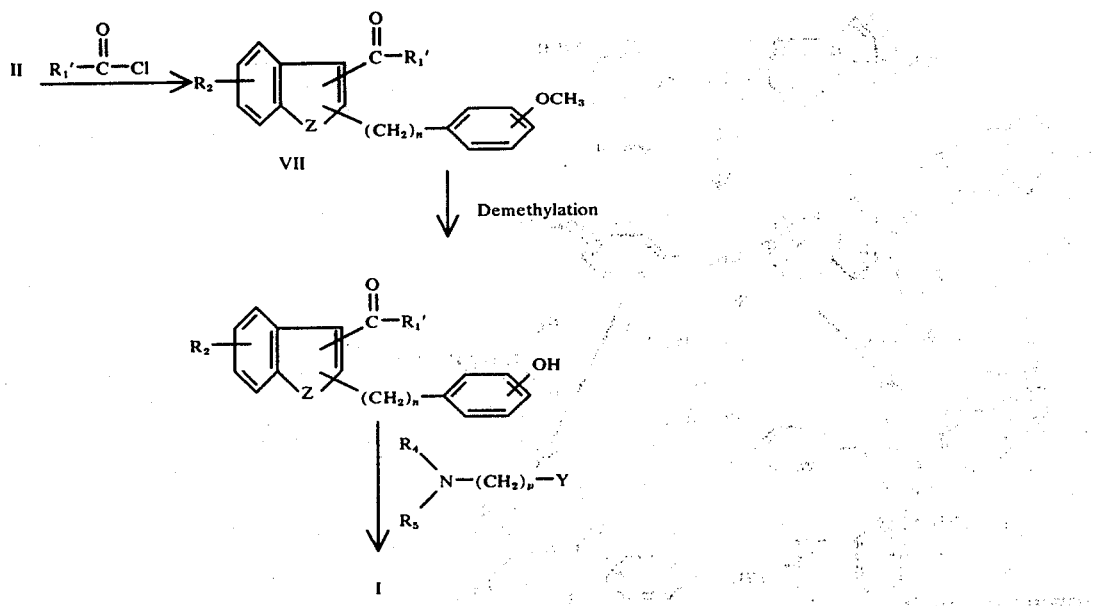

where $R_2$, $R_4$, $R_5$, p, n, Y and Z are defined as above and $R_1'$ is phenyl, halophenyl, dihalophenyl, trihalophenyl, lower alkylphenyl, di-lower alkylphenyl or tri-lower alkylphenyl.

Thus, a methoxyphenyl or methoxybenzyl benzofuran or benzothiophene of formula II is acylated as previously described to give the methoxyphenyl- or methoxybenzyl-benzoyl benzofuran or benzothiophene VII. Demethylation of VII followed by reaction with a substituted aminoalkyl halide, tosylate or mesylate as described above gives the corresponding compounds of this invention.

The corresponding compounds of formula I where $R_6$ is hydroxy are prepared according to Scheme 3:

SCHEME 3

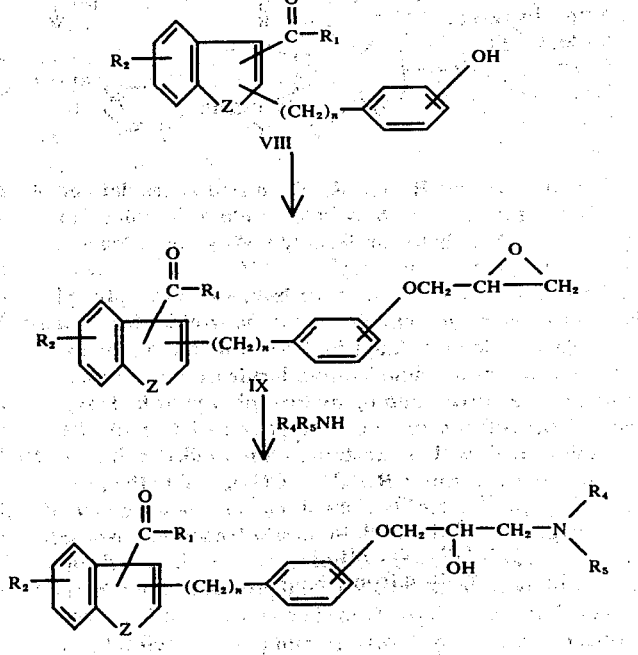

The terms $R_1$, $R_2$, $R_4$, $R_5$, n and Z are defined as above.

As shown in the above procedure, a hydroxyphenyl benzofuranyl or benzothiophenyl ketone of formula VIII is converted to the epoxy intermediate IX which is then opened by reaction with an appropriate amine ($R_4R_5NH$). The epoxy intermediates of formula IX are prepared by reaction of a compound of formula VIII with an epihalohydrin such as epichlorohydrin or epibromohydrin in the presence of a base such as sodium hydroxide or potassium carbonate in a solvent such as water, ethanol or acetone.

The ring opening of the epoxy intermediates of formula IX is preferably carried out in a minimum amount of a solvent such as ethanol or with excess amine as solvent in a pressure bomb at from about 25° to about 125° C., preferably at 100° C., for from 1 to about 6 hours, preferably from 3 to 4 hours.

When Z is sulfur, the benzothiophenes of formula I are preferably prepared by acylation of a methoxyphenyl or methoxybenzyl benzothiophene as previously described to give a methoxyphenyl- or methoxybenzyl-benzoyl benzothiophene which is then demethylated to the corresponding hydroxy compound. Reaction of the hydroxyphenyl- or hydroxybenzyl-benzoyl benzothiophene with a substituted aminoalkyl halide or tosylate, a dihaloalkane followed by treatment of the product formed with an amine of the formula $R_4R_5NH$ where $R_4$ and $R_5$ are defined as above or with an epihalohydrin followed by ring opening with an amine ($R_4R_5NH$) gives the benzothiophene compounds of formula I.

The products of formula I are isolated and purified as such by standard techniques including solvent extraction, crystallization and chromatographic methods or as the corresponding acid addition salts which are also objects of this invention. The salts are formed with organic and inorganic acids according to methods known to the art. Thus, a solution of the amine in ether or an alcohol such as methanol or ethanol is treated with a solution of an organic or inorganic acid in an aqueous miscible solvent, such as acetone or ethanol, with isolation of the salt by concentration and cooling or in an aqueous immiscible solvent, such as ether, with the desired salt separating directly. Exemplary of such organic salts are those with maleic, fumaric, benzoic, ascorbic, pamoic, succinic, hexamic, oxalic, bismethylenesalicyclic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids as well as with the 8-halotheophyllines, for example, 8-bromotheophylline. Exemplary of such inorganic salts are those with hydrochloric, hydrobromic, sulfuric, sulfamic, phosphoric and nitric acids. Of course, these salts may also be prepared by the classical method of double decomposition of appropriate salts which is well known to the art. The salts may be purified by the standard methods described above.

The substituted benzofuranyl ketone starting materials of Scheme 3(VIII) are prepared by standard methods for the synthesis of benzofurans. For example, an acid chloride of the formula

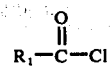

is used to acylate a methoxyphenyl or methoxybenzyl substituted benzofuran nucleus by known procedures, for example in the presence of stannic chloride or aluminum chloride in a solvent such as methylene chloride, carbon disulfide or nitrobenzene. The resulting methoxyphenyl or methoxybenzyl benzofuranyl ketone is then demethylated by known methods, for example by use of pyridine hydrochloride or boron tribromide.

The methoxyphenyl or methoxybenzyl substituted benzofuran nuclei used as starting materials in Schemes 1 and 2 (II) and in the preparation of the compounds of formula VIII are either known to the art or are prepared by one of the general methods for the snythesis of benzofurans described by Buu-Hoi et al., *J. Chem. Soc.* 3693 (1955), 625 (1957), 2593 (1957) and 173 (1964); Tanaka, *J. Amer. Chem. Soc.* 73:872 (1951); Bisagni et al., *J. Chem. Soc.* 3688 (1955); Grinev et al., *Zhur. Obshchei Khim.* 27:1087 (1957); Castro et al., *J. Org. Chem.* 28:3313 (1963), 31:4071 (1966); Rodd, *Chemistry of Carbon Compounds* Vol. IV-A, 168–191; Mustafa, *The Chemistry of Heterocyclic Compounds Vol. 29, Benzofurans* and French Pat. No. 1,537,206. Representative methods for preparing these starting materials are exemplified hereinafter.

Alternatively, the methoxybenzyl substituted benzofuran starting materials (II) are prepared by addition of a phenyl magnesium halide to a cyanobenzofuran followed by hydrolysis and reduction of the product with a reducing agent such as hydrazine hydrate.

The methoxyphenyl or methoxybenzyl substituted benzothiophene nuclei are either known to the art or are prepared by methods similar to those used to prepare the corresponding benzofuran nuclei. For example, these starting materials are prepared by addition of a phenyl magnesium halide to a cyanobenzothiophene followed by hydrolysis and reduction of the product with a reducing agent such as hydrazine hydrate or by reaction of a substituted thiophenol with α-bromo-p-methoxyacetophenone with subsequent cyclization of the product thus formed, for example by treatment with polyphosphoric acid.

When $R_1$ contains an alkoxy group(s) and/or $R_2$ is alkoxy, the corresponding compounds of formula 1 in which

is in the 3-position and $R_6$ is hydrogen are preferably prepared as shown in Scheme 4 in which the terms $R_1$, $R_2$, $R_4$, $R_5$, n, p and Z are as defined above:

SCHEME 4

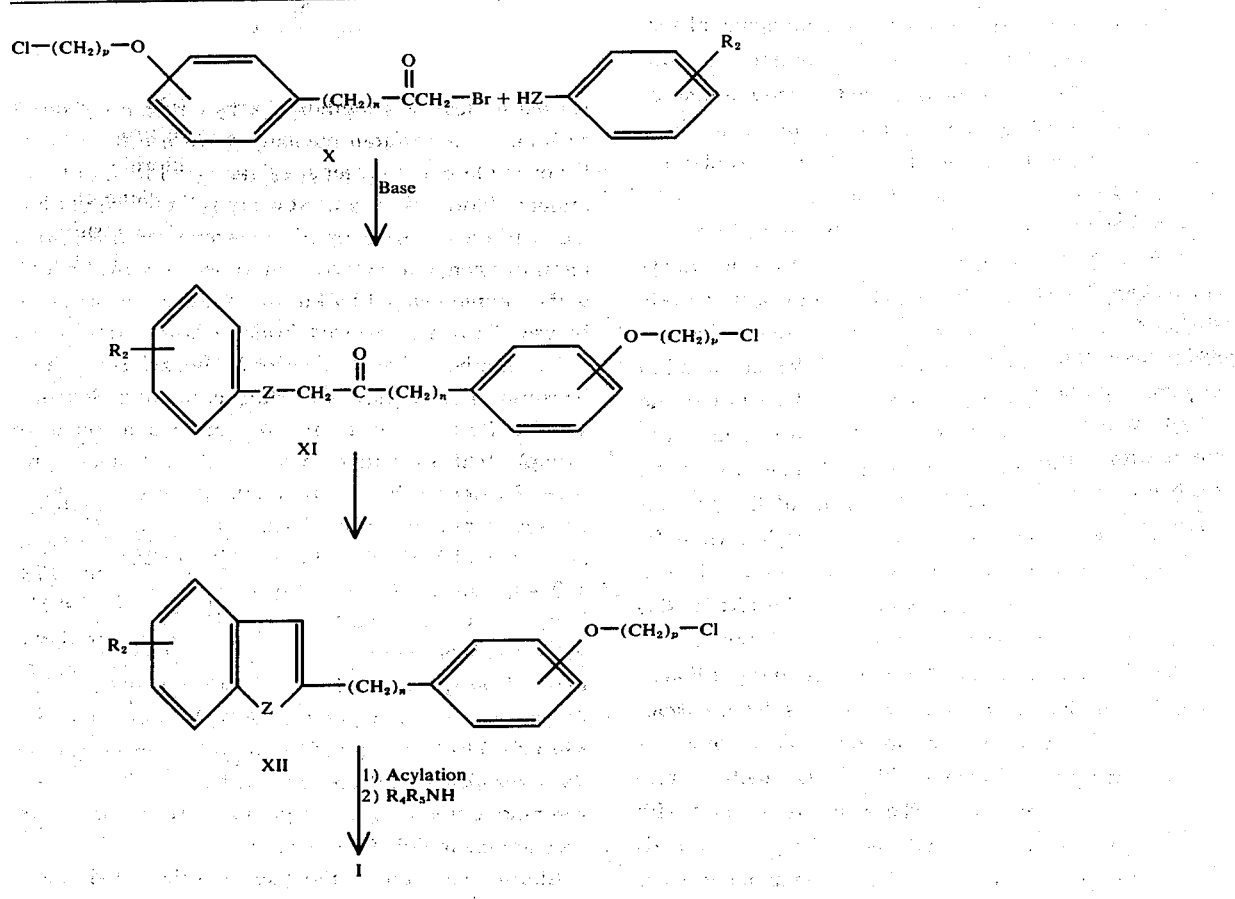

Thus, reaction of a substituted phenol or thiophenol with a bromomethyl chloroalkoxyphenyl or benzyl ketone of formula X in the presence of a base such as potassium carbonate in a solvent such as acetone gives the corresponding compound of formula XI. Cyclization of XI, for example with polyphosphoric acid, produces benzofuran or benzothiophene XII which, upon acylation followed by reaction of the product with an amine ($R_4R_5NH$) as previously described, gives the corresponding compounds of formula I.

The bromomethyl chloroalkoxyphenyl or benzyl ketones of formula X are either known to the art or are prepared by reaction of the corresponding bromomethyl hydroxyphenyl or benzyl ketone with a chloroalkyl halide of the formula $Cl-(CH_2)_p-X$. The bromomethyl hydroxyphenyl or benzyl ketones are obtained from hydroxyphenylacetyl or hydroxybenzoyl halides, preferably chlorides, according to known procedures such as reaction of a hydroxyphenylacetyl or hydroxybenzoyl chloride with diazomethane and hydrogen bromide.

The acid chloride acylating agents,

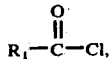

are either known to the art or are prepared by standard methods, for example by treatment of the corresponding benzoic acid with thionyl chloride or phosphorus pentachloride.

The coronary vasodilator activity and hypotensive effects of the compounds of this invention are demonstrated in dogs by an increase in coronary blood flow with concomitant decrease of mean arterial blood pressure upon intravenous administration of doses of from about 0.32 to about 5.0 mg./kg. These parameters are measured as follows:

Adult mongrel dogs (13–16 kg.) are pretreated with 2 mg./kg. s.c. of morphine sulfate followed in one hour by intravenous administration of 1–1.5 ml./kg. of an aqueous solution containing 1.5% chloralose and 20% urethane. Supplemental doses of morphine and chloralose-urethane are given to maintain an adequate and uniform depth of anesthesia.

A carotid artery is catheterized and connected to a Sanborn pressure transducer to measure arterial blood pressure. A femoral vein is also catheterized for administering a solution of the test compound or its salt and supplemental anesthesia. A left thoractomy is made at the fourth or fifth intercostal space, the lung is displaced, the pericardium is opened and the left circumflex coronary artery is isolated for measurement of coronary blood flow, a "snare" being placed around the artery distally to obtain zero flow. Coronary blood flow is measured with a Statham electromagnetic flowmeter and Flo-Probe (MDS).

In addition, the particularly preferred compounds of formula I, namely 2-[4'-(2-diethylaminoethoxy)-phenyl]-3-(3',5'-dimethylbenzoyl)benzofuran, 2-[4'-(2-diethylaminoethoxy)phenyl]-3-(3',4',5'-trimethylbenzoyl)benzofuran, 5-chloro-2-[4'-(2-diethylaminoethoxy)phenyl]-3-(3',5'-dimethylbenzoyl)benzofuran, 3-(3',5'-dimethylbenzoyl)-2-[4'-(2-N-pyrrolidinoethoxy)phenyl]benzofuran, 3-(3',5'-dimethylbenzoyl)-2-[4'-(2-N-piperidinoethoxy)phenyl]benzofuran and 2-(4'-chlorobenzoyl)-3-[4'-(2-hydroxy-3-isopropylaminopropoxy)phenyl]benzofuran also inhibit or attenuate the chronotropic effect of isoproterenol-induced tachycardia upon administration to dogs at doses of from about 1.25 to about 10.0 mg./kg. i.v. Abad et al. [Acta Pharmacol. et Toxicol. 25:85 (1967)] have correlated the inhibition of isoproterenol-induced tachycardia to utility as an anti-anginal agent.

The pharmacologically active compounds of this invention may be administered orally or parenterally in an amount to produce the desired activity.

Preferably the compounds are administered in conventional dosage unit forms prepared by combining an appropriate dose of the compound with standard pharmaceutical carriers. The dosage units will contain the active ingredient in an amount of from about 100 mg. to about 600 mg., preferably 150 mg. to 300 mg. per dosage unit.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or an aqueous or nonaqueous liquid suspension.

The pharmaceutical compositions are prepared by conventional techniques involving procedures such as mixing, granulating and compressing when necessary or variously mixing and dissolving the ingredients as appropriate to the desired composition.

The method of producing coronary vasodilator activity in accordance with this invention comprises administering internally to an animal an effective amount of a compound of this invention. The compound will preferably be administered in a dosage unit form as described above orally or parenterally, the oral route being preferred. Advantageously equal doses will be administered one to two times daily with the daily dosage regimen being from about 200 mg. to about 1200 mg., preferably from about 300 mg. to about 600 mg. When the method described above is carried out, coronary vasodilator activity is produced.

One skilled in the art will recognize that in determining the amounts of the compound needed to produce the desired pharmacological effect without toxic side effects, the activity of the compound as well as the size of the host animal must be considered.

The following examples illustrate the invention but are not to be construed as limiting the scope thereof. Temperatures are in degrees Centigrade unless otherwise stated.

When formed, acid addition salts may be converted to the corresponding free amines by treating a solution of the salt in a solvent such as water, a chloroform-water or a benzene-water mixture with a base such as 10% aqueous sodium hydroxide, sodium carbonate or sodium bicarbonate until basic followed by extraction of the amine into benzene or chloroform. Salts other than hydrochlorides may be converted to the corresponding hydrochloric acid salts by passing a solution of the salt in methanol or ethanol through an Amberlite IRA-401 chloride ion exchange column.

EXAMPLE 1

2-[4'-(3-Diethylaminopropoxy)phenyl]-3-(4'-methylbenzoyl)-benzofuran

To a cooled (0°) mixture of 4.07 g. (0.018 mol.) of 2-p-methoxyphenylbenzofuran and 4.17 g. (0.027 mol.) of p-toluic acid chloride in 100 ml. of methylene chloride was added dropwise 11.25 g. (0.043 mol.) of stannic chloride. The reaction mixture was stirred for 1.5 hours at 0°, then for 0.5 hour at 25°. The mixture was poured into water and stirred vigorously, the layers were separated and the organic phase was washed with saturated aqueous sodium bicarbonate, dried (MgSO$_4$) and concentrated to give 2-p-methoxyphenyl-3-p-methylbenzoylbenzofuran.

2-p-Methoxyphenyl-3-p-methylbenzoylbenzofuran (4.9 g., 0.014 mol.) was combined with 50 g. of freshly distilled pyridine hydrochloride and the mixture was heated at 180°–190° for 4.5 hours. The hot mixture was poured with stirring onto an ice-5% aqueous hydrochloric acid mixture and the precipitate formed was extracted into ether. The ether solution was dried (MgSO$_4$) and concentrated under reduced pressure to give 2-p-hydroxyphenyl-3-p-methylbenzoylbenzofuran.

To a solution of 0.177 g. (7.7 g.-atom) of sodium dissolved in 25 ml. of dry methanol was added a solution of 2.4 g. (7.3 mmol.) of 2-p-hydroxyphenyl-3-p-methylbenzoylbenzofuran in 75 ml. of toluene and 10 ml. of methanol. The mixture was refluxed for 15 minutes, then the methanol was removed by distillation. A solution of 1.15 g. (7.7 mmol.) of 3-diethylaminopropyl chloride in 25 ml. of toluene was then added and the resulting mixture was refluxed for 6 hours. After cooling, the reaction mixture was filtered and the filtrate was concentrated to give the title compound.

The title compound was dissolved in dry ether and an etheral solution of hydrochloric acid was added to precipitate the benzofuran hydrochloride salt. The ether was decanted and the crude salt was dissolved in chloroform and chromatographed on silica with chloroform and chloroform containing 10% methanol as the eluant to give 2-[4'-(3-diethylaminopropoxy)-phenyl]-3-(4'-methylbenzoyl)benzofuran hydrochloride, m.p. 84°–87°.

EXAMPLE 2

3-Benzoyl-2-[4'-(2-diethylaminoethoxy)phenyl]benzofuran

When benzoyl chloride was substituted in the procedure of Example 1 for p-toluic acid chloride, 3-benzoyl-2-p-methoxyphenylbenzofuran was obtained.

Demethylation of 3-benzoyl-2-p-methoxyphenylbenzofuran followed by reaction of the 3-benzoyl-2-p-hydroxyphenylbenzofuran thus obtained with 2-diethylaminoethyl chloride according to the procedure of Example 1 gave the title compound.

3-Benzoyl-2-[4'-(2-diethylaminoethoxy)phenyl]benzofuran was converted to the corresponding hydrochloride as described in Example 1.

EXAMPLE 3

3-(4'-Chlorobenzoyl)-2-[4'-(2-diethylaminoethoxy)-phenyl]benzofuran

Reaction of p-chlorobenzoyl chloride with 2-p-methoxyphenylbenzofuran gave 3-p-chlorobenzoyl-2-p-methoxyphenylbenzofuran.

Demethylation of 3-p-chlorobenzoyl-2-p-methoxyphenylbenzofuran followed by reaction of the 3-p-chlorobenzoyl-2-p-hydroxyphenylbenzofuran thus obtained with 2-diethylaminoethyl chloride according to the procedure of Example 1 gave the title compound.

The corresponding hydrochloride of 3-(4'-chlorobenzoyl)-2-[4'-(2-diethylaminoethoxy)phenyl]-benzofuran was prepared as described in the procedure of Example 1, m.p. 155°–165°.

EXAMPLE 4

3-(4'-Chlorobenzoyl)-2-[4'-(3-diethylaminopropoxy)-phenyl]-benzofuran

When 3-p-chlorobenzoyl-2-p-hydroxyphenylbenzofuran was reacted with 3-diethylaminopropyl chloride by the procedure of Example 1, the title compound was obtained.

The corresponding hydrochloric acid salt of 3-(4'-chlorobenzoyl)-2-[4'-(3-diethylaminopropoxy)-phenyl]benzofuran was prepared as described in the procedure of Example 1, m.p. 90°–94°.

EXAMPLE 5

3-p-Anisoyl-2-[4'-(3-diethylaminopropoxy)phenyl]-benzofuran

A solution of 4.9 g. (0.023 mol.) of 2-p-hydroxyphenylbenzofuran in 75 ml. of toluene and 5 ml. of methanol was added to a sodium methoxide solution prepared by dissolving 0.54 g. (0.023 g.-atom) of sodium in 25 ml. of methanol. The mixture was refluxed for 15 minutes, then the methanol was removed by distillation and 3.48 g. (0.023 mol.) of diethylaminopropyl chloride was added and the resulting reaction mixture was refluxed for four hours. The mixture was filtered and the filtrate concentrated under reduced pressure to give 2-[4'-(3-diethylaminopropoxy)-phenyl]benzofuran, m.p. 86°–88°.

To a solution of 1.02 g. (0.006 mol.) of p-anisoyl chloride in 75 ml. of methylene chloride was added 2.0 g. (6.2 mmol.) of the hydrochloride salt of 2-[4'-(3-diethylaminopropoxy)phenyl]benzofuran. The reaction mixture was cooled to 0°, 3.3 ml. (0.024 mol.) of stannic chloride was added and the resulting mixture was stirred for 10 minutes at 0° then for 2.75 hours at 25°. The mixture was then poured into water and stirred vigorously. The layers were separated and the organic phase was washed with 10% aqueous sodium carbonate solution and water, dried (MgSO$_4$) and concentrated to give the title compound as an oil.

The hydrochloric acid salt of 3-p-anisoyl-2-[4'-(3-diethylaminopropoxy)phenyl]benzofuran was prepared as described in Example 1.

EXAMPLE 6

2-[4'-(3-Diethylaminopropoxy)phenyl]-3-(3',5'-dimethylbenzoyl)benzofuran

To a suspension of 2.0 g. (6.2 mmol.) of the hydrochloride salt of 2-[4'-(3-diethylaminopropoxy)-phenyl]benzofuran in 10 ml. of nitrobenzene was added a solution of 1.84 g. (13.9 mmol.) of aluminum chloride in 20 ml. of nitrobenzene. The solution was cooled to 0° and 1.24 g. (7.4 mmol.) of 3,5-dimethylbenzoyl chloride was added. The reaction mixture was stirred at 0° for 30 minutes then at 25° for 1.5 hours, after which time it was poured into water and the nitrobenzene was removed by steam distillation. The aqueous solution was extracted with ether, made alkaline with aqueous sodium carbonate solution and again extracted with ether. The etheral solution was dried (MgSO$_4$) and concentrated to give the title compound.

Addition of an ether solution of hydrochloric acid to a solution of the title compound in ether gave the corresponding hydrochloride salt as an oil which was purified by column chromatography and crystallized from ethyl acetate, m.p. 130°–138°.

EXAMPLE 7

2-[4'-(2-Diethylaminoethoxy)phenyl]-3-(3',5'-dimethylbenzoyl)benzofuran

To a cooled (0°) solution of 14.0 g. (0.105 mol.) of aluminum chloride in 100 ml. of nitrobenzene was added 11.2 g. (0.05 mol.) of 2-p-methoxyphenylbenzofuran followed immediately by 10.0 g. (0.06 mol.) of 3,5-dimethylbenzoyl chloride. The reaction mixture was stirred at 0° for 12 minutes (until the red color began to turn reddish-brown) then poured into water. The aqueous mixture was steam distilled to remove nitrobenzene and the residue was dissolved in methylene chloride. The methylene chloride solution was washed with aqueous sodium carbonate and saturated sodium chloride solution, dried (MgSO$_4$) and concentrated at reduced pressure to give a residue which was purified by column chromatography to give 2-p-methoxyphenyl-3-(3',5'-dimethylbenzoyl)benzofuran which was then crystallized from ethanol.

2-p-Methoxyphenyl-3-(3',5'-dimethylbenzoyl)benzofuran was demethylated to 2-p-hydroxyphenyl-3-(3',5'-dimethylbenzoyl)benzofuran with pyridine hydrochloride as described in Example 1.

2-p-Hydroxyphenyl-3-(3',5'-dimethylbenzoyl)benzofuran (5.25 g., 15.3 mmol.) was dissolved in 200 ml. of dry acetone and 10.5 g. (0.076 mol.) of potassium carbonate and 2.10 g. (15.3 mmol.) of 2-diethylaminoethyl chloride were added. The reaction mixture was refluxed for three hours, then it was cooled and filtered. The filtrate was concentrated at reduced pressure to give the title compound as an oil.

The title compound was dissolved in dry ether to which solution was added an ether solution of hydrochloric acid to give the corresponding hydrochloric acid salt, m.p. 155°–157°.

EXAMPLE 8

3-(3',5'-Dichlorobenzoyl)-2-[4'-(2-diethylaminoethoxy)phenyl]benzofuran

A solution of 13.4 g. (0.07 mol.) of 3,5-dichlorobenzoic acid and 10.7 g. (0.09 mol.) of thionyl chloride in 60 ml. of methylene chloride was refluxed on a steam bath for two hours. Concentration under reduced pressure and distillation of the residue gave 3,5-dichlorobenzoyl chloride.

Substitution of 3,5-dichlorobenzoyl chloride in the procedure of Example 7 for 3,5-dimethylbenzoyl chloride followed by demethylation of the 3-(3',5'-dichlorobenzoyl)-2-p-methoxyphenylbenzofuran as described above gave 3-(3',5'-dichlorobenzoyl)-2-p-hydroxyphenylbenzofuran.

Treatment of 3-(3',5'-dichlorobenzoyl)-2-p-hydroxyphenylbenzofuran with 2-diethylaminoethyl chloride according to the procedure of Example 7 gave the title compound.

The title compound was converted to the corresponding hydrochloride salt as previously described, m.p. 165°–168°.

EXAMPLE 9

2-[4'-(2-Dimethylaminoethoxy)phenyl]-3-(3',5'-dimethylbenzoyl)benzofuran

Reaction of 2-p-hydroxyphenyl-3-(3',5'-dimethylbenzoyl)benzofuran with 2-dimethylaminoethyl chloride by the procedure described in Example 7 gave the title compound.

The title compound was converted to the corresponding hydrochloric acid salt as described in Example 7, m.p. 132°–135°.

EXAMPLE 10

2-[4'-(2-Diethylaminoethoxy)phenyl]-3-(3',4',5'-trimethylbenzoyl)benzofuran

By using 3,4,5-trimethylbenzoyl chloride, prepared from treatment of 3,4,5-trimethylbenzoic acid with thionyl chloride as described hereinabove, in place of 3,5-dimethylbenzoyl chloride in the procedure of Example 7, the title compound was ultimately obtained.

Treatment of the title compound with an ethereal solution of hydrochloric acid as described in Example 7 gave the corresponding hydrochloride salt, m.p. 171°–173°.

EXAMPLE 11

2-[4'-(2-Diethylaminoethoxy)phenyl]-3-(3',5'-dimethoxybenzoyl)benzofuran

A mixture of 10.5 g. (0.05 mol.) of 2-p-hydroxyphenylbenzofuran and 47 g. (0.25 mol.) of 1,2-dibromoethane in 200 ml. of 3-pentanone containing 46 g. (0.3 mol.) of potassium carbonate was heated at 100° for 12 hours. The mixture was filtered while hot and the solid remaining was washed with hot acetone. The combined filtrate and washings were concentrated to give 2-[4'-(2-bromoethoxy)phenyl]benzofuran.

To a mixture of 2.93 g. (0.022 mol.) of aluminum chloride and 2.21 g. (0.011 mol.) of 3,5-dimethoxybenzoyl chloride in 50 ml. of nitrobenzene at 0° was added to 3.19 g. (0.010 mol.) of 2-[4'-(2-bromoethoxy)phenyl]benzofuran. The reaction mixture was stirred for one hour then poured into water. The nitrobenzene was steam distilled from the aqueous mixture and the residue was extracted with chloroform. The extract was dried (MgSO₄) and concentrated under reduced pressure to give, after chromatography, 2-[4'-(2-bromoethoxy)phenyl]-3-(3',5'-dimethoxybenzoyl)benzofuran.

A solution of 1.59 g. (3.3 mmol.) of 2-[4'-(2-bromoethoxy)phenyl-3-(3',5'-dimethoxybenzoyl)benzofuran and 8 ml. of diethylamine in 100 ml. of ethanol was refluxed for 18 hours. The reaction mixture was concentrated under reduced pressure and 10% aqueous sodium hydroxide and ether were added to the residue. The mixture was shaken until complete dissolution and the layers were separated. The ether layer was dried (MgSO₄) and concentrated under reduced pressure to give the title compound.

Treatment of a solution of the title compound with an ether solution of hydrochloric acid as described in the procedure of Example 1 gave the corresponding hydrochloric acid salt, m.p. 163°–165°.

EXAMPLE 12

2-[4'-(2-Diethylaminoethoxy)phenyl]-3-(3',5'-dimethyl-4'-methoxybenzoyl)benzofuran When an equivalent amount of 3,5-dimethyl-4-methoxybenzoyl chloride, prepared from 3,5-dimethyl-4-methoxybenzoic acid and thionyl chloride as previously described, was substituted in the procedure of Example 11 for 3,5-dimethoxybenzoyl chloride, 2-[4'-(2-bromoethoxy)phenyl]-3-(3',5'-dimethyl-4'-methoxybenzoyl)benzofuran was obtained.

Reaction of 2-[4'-(2-bromoethoxy)phenyl]-3-(3',5'-dimethyl-4-methoxybenzoyl)benzofuran with diethylamine as described in Example 11 gave the title compound.

The title compound was converted to the corresponding hydrochloride salt by the procedure of Example 1, m.p. 130°–133°.

EXAMPLE 13

3-(3',5'-Dimethylbenzoyl)-2-[4'-(2-di-n-propylaminoethoxy(phenyl]benzofuran

Substitution of an equivalent amount of 3,5-dimethylbenzoyl chloride for 3,5-dimethoxybenzoyl chloride in the procedure of Example 11 gave 2-[4'-(2-bromoethoxy)phenyl]-3-(3',5'-dimethylbenzoyl)benzofuran.

Reaction of 2-[4'-(2-bromoethoxy)phenyl]-3-(3',5'-dimethylbenzoyl)benzofuran with di-n-propylamine as described in Example 11 gave the title compound.

The title compound was converted to the corresponding hydrochloride salt by the procedure of Example 1, m.p. 158°–160°.

EXAMPLE 14

When an equivalent amount of a substituted benzoic acid listed below:
p-bromobenzoic acid
m-fluorobenzoic acid
3,5-dibromobenzoic acid
2,3-difluorobenzoic acid
2,3,5-trichlorobenzoic acid
is used as a starting material in Example 8 in place of 3,5-dichlorobenzoic acid, there are obtained the following benzofurans:
3-p-bromobenzoyl-2-p-methoxyphenylbenzofuran
3-m-fluorobenzoyl-2-p-methoxyphenylbenzofuran
3-(3',5'-dibromobenzoyl)-2-p-methoxyphenylbenzofuran
3-(2',3'-difluorobenzoyl)-2-p-methoxyphenylbenzofuran
3-(2',3',5'-trichlorobenzoyl)-2-p-methoxyphenylbenzofuran.

Demethylation of the above listed 2-p-methoxyphenyl benzofurans with pyridine hydrochloride followed by reaction of the 2-p-hydroxyphenyl benzofurans thus formed with 2-diethylaminoethyl chloride as described in Example 1 gives the following compounds of this invention:

3-(4'-bromobenzoyl)-2-[4'-(2-diethylaminoethoxy)-phenyl]benzofuran

2-[4'-(2-diethylaminoethoxy)phenyl]-3-(3'-fluorobenzoyl)benzofuran 3-(3',5'-dibromobenzoyl)-2-[4'-(2-diethylaminoethoxy(phenyl]benzofuran 2-[4'-(2-diethylaminoethoxy)phenyl]-3-(2',3'-difluorobenzoyl)benzofuran 2-[4'-(2-diethylaminoethoxy)phenyl]-3-(2',3',5'-trichlorobenzoyl)benzofuran.

EXAMPLE 15

2-[4'-(2-Diethylaminoethoxy)benzyl]-3-(3',5'-dimethylbenzoyl)benzofuran

To 11.0 g. (0.09 mol.) of salicylaldehyde in 30 ml. of dry methanol was added 5.1 g. (0.09 mol.) of potassium hydroxide dissolved in 50 ml. of methanol. The solution was refluxed for 10 minutes and 20.5 g. (0.09 mol.) of α-bromo-p-methoxyacetophenone dissolved in 50 ml. of warm methanol was added dropwise but rapidly over a 10 minute interval. The resulting solution was refluxed for one hour, then filtered and concentrated. The residue was dissolved in ether and the ether solution was washed with water. The aqueous washings were extracted twice with ether and the ethereal extracts were combined, reduced in volume, refluxed with decolorizing carbon, filtered, dried (MgSO₄) and concentrated to give 2-(4'-methoxybenzoyl)benzofuran which was recrystallized from isopropanol, m.p. 93°–94°.

Hydrazine hydrate (28.0 g., 0.42 mol.) is added to a solution of 38.1 g. (0.16 mol.) of 2-(4'-methoxybenzoyl)benzofuran in 400 ml. of ethanol and the reaction mixture is refluxed overnight. The solution is concentrated, chloroform is added and the chloroform solution is washed with saturated aqueous sodium chloride, dried (MgSO₄) and concentrated to yield the corresponding hydrazone. The hydrazone is dissolved in 100 ml. of dry dimethyl sulfoxide and added dropwise over a four hour interval to a slurry of 36.4 g. (0.32 mol.) of potassium t-butoxide in 100 ml. of dry dimethyl sulfoxide. The reaction mixture is poured into 500 ml. of water and the aqueous solution is extracted with chloroform. The extracts are washed with water, dried (MgSO₄) and concentrated under reduced pressure to give 2-(4'-methoxybenzyl)benzofuran which is purified by chromatography.

Substitution of an equivalent amount of 2-(4'-methoxybenzyl)benzofuran in the procedure of Example 7 for 2-p-methoxyphenylbenzofuran followed by the subsequent synthetic steps described therein gives the title compound.

EXAMPLE 16

2-[2'-(3-Diethylaminopropoxy)benzyl]-3-4'-methylbenzoyl)benzofuran 2-(2'-Methoxybenzyl)benzofuran is prepared as described in the procedure of Example 15 by the use of α-bromo-o-methoxyacetophenone as a starting material in place of α-bromo-p-methoxyacetophenone.

Substitution of an equivalent amount of 2-(2'-methoxybenzyl)benzofuran in the procedure of Example 1 for 2-p-methoxyphenylbenzofuran followed by the subsequent synthetic steps described therein gives the title compound.

EXAMPLE 17

2-[3'-(2-Diethylaminoethoxy)phenyl]-3-(3',5'-dimethylbenzoyl)benzofuran

When an equivalent amount of 2-m-methoxyphenylbenzofuran was used as a starting material in the procedure of Example 7 in place of 2-p-methoxyphenylbenzofuran. 2-m-methoxyphenyl-3-(3',5'-dimethylbenzoyl)benzofuran was obtained.

Demethylation of 2-m-methoxyphenyl-3-(3',5'-dimethylbenzoyl)benzofuran followed by reaction of the 2-m-hydroxyphenyl-3-(3',5'-dimethylbenzoyl)benzofuran thus formed with 2-diethylaminoethyl chloride as described in Example 7 gave the title compound which was converted to the corresponding hydrochloride salt as described hereinabove, m.p. 156°–158°.

EXAMPLE 18

5-Chloro-2-[4'-(2-diethylaminoethoxy)phenyl]-3-(3',5'-dimethylbenzoyl)benzofuran Substitution of an equivalent amount of 5-chloro-2-p-methoxyphenylbenzofuran for 2-p-methoxyphenylbenzofuran in the procedure of Example 7 followed by the subsequent synthetic steps described therein gave the title compound as the final product.

The title compound was converted to the corresponding hydrochloride salt by procedures described hereinabove, m.p. 161°–162°.

EXAMPLE 19

4-Chloro-2-[4'-(2-diethylaminoethoxy)benzyl]-3-(3',5'-dimethylbenzoyl)benzofuran When an equivalent amount of 6-chlorosalicylaldehyde is used as a starting material in the procedure of Example 15 in place of salicylaldehyde and the product 4-chloro-2-(4'-methoxybenzoyl)benzofuran is reduced with hydrazine hydrate, 4-chloro-2-(4'-methoxybenzyl)benzofuran is obtained.

Substitution of an equivalent amount of 4-chloro-2-(4'-methoxybenzyl)benzofuran in the procedure of Example 7 for 2-p-methoxyphenylbenzofuran followed by the subsequent synthetic steps described therein gives the title compound as the final product.

EXAMPLE 20

6-Chloro-2-[4'-(2-diethylaminoethoxy)phenyl]-3-(3',5'-dimethylbenzoyl)benzofuran To a stirred solution of 13.88 g. (0.105 mol.) of p-ethynylanisole in 500 ml. of ethanol is added a solution of 20.0 g. (0.105 mol.) of cuprous iodide in aqueous ammonia. The reaction mixture is stirred for 15 minutes and the precipitate formed is collected by filtration and washed with copious amounts of water, ethanol and ether to give cuprous p-methoxyphenylacetylide.

A flask containing 2.14 g. (0.011 mol.) of cuprous p-methoxyphenylacetylide in 80 ml. of dimethylformamide is thoroughly flushed with nitrogen. A solution of 2.28 g. (0.011 mol.) of 2-bromo-5-chlorophenol in 20 ml. of dimethylformamide is added under nitrogen and the reaction mixture is stirred and warmed at 120° for 24 hours. The mixture is then filtered and the filtrate is concentrated in vacuo. The residue is dissolved in chloroform, refiltered and the filtrate is washed with water and concentrated to give 6-chloro-2-p-methoxyphenylbenzofuran.

Substitution of an equivalent amount of 6-chloro-2-p-methoxyphenylbenzofuran in the procedure of Example 7 followed by the subsequent synthetic steps of demethylation and reaction of the product with 2-diethylaminoethyl chloride as described therein gives the title compound.

EXAMPLE 21

Reaction of a substituted phenol listed below:
2-bromo-6-ethylphenol
2-bromo-4-fluorophenyl
2-bromo-4-methylphenol
with cuprous p-methoxyphenylacetylide according to the procedure described in Example 20 gives the following substituted 2-p-methoxyphenylbenzofurans:
7-ethyl-2-p-methoxyphenylbenzofuran
5-fluoro-2-p-methoxyphenylbenzofuran
5-methyl-2-p-methoxyphenylbenzofuran.

Substitution of a 2-p-methoxyphenylbenzofuran listed above in the procedure of Example 7 for 2 -p-methoxyphenylbenzofuran followed by the synthetic steps of demethylation of the substituted 2-p-methoxyphenyl-3(3′,5′-dimethylbenzoyl)benzofuran and treatment of the product thus formed with 2-diethylaminoethyl chloride as described therein gives the following compounds of this invention:
7-ethyl-2-[4′-(2-diethylaminoethoxy)phenyl]-3-(3′,5′-dimethylbenzoyl)benzofuran
2-[4′-(2-diethylaminoethoxy)phenyl]-5-fluoro-3-(3′,5′-dimethylbenzoyl)benzofuran
2-[4′-(2-diethylaminoethoxy)phenyl]-5-methyl-3-(3′,5′-dimethylbenzoyl)benzofuran.

EXAMPLE 22

Use of a benzoyl chloride listed below, prepared from treatment of the corresponding substituted benzoic acid with thionyl chloride as described in Example 8:
3,5diethylbenzoyl chloride
4-n-propylbenzoyl chloride
4-t-butylbenzoyl chloride
3,5-di-t-butylbenzoyl chloride
as a starting material in place of 3,5-dimethylbenzoyl chloride in the procedure of Example 7 gives, as final products, the following compounds of this invention:
2-[4′-(2-diethylaminoethoxy)phenyl]-3-(3′,5′-diethylbenzoyl)benzofuran
2-[4′-(2-diethylaminoethoxy)phenyl]-3-(4′-n-propylbenzoyl)benzofuran
3-(4′-t-butylbenzoyl)-2-[4′-(2-diethylaminoethoxy)phenyl]benzofuran
3-(3′,5′-di-t-butylbenzoyl)-2-[4′-(2-diethylaminoethoxy)phenyl]benzofuran.

EXAMPLE 23

Use of a benzoyl chloride listed below, prepared from treatment of the corresponding substituted benzoic acid with thionyl chloride as described in Example 8:
3,4-diethoxybenzoyl chloride
3-n-propoxybenzoyl chloride
4-n-butoxybenzoyl chloride
3,5-di-t-butoxybenzoyl chloride
3,4,5-trimethoxybenzoyl chloride
2,5-dimethoxy-4-methylbenzoyl chloride as a starting material in place of 3,5-dimethoxybenzoyl chloride in the procedure of Example 11 gives, as final products, the following compounds of this invention:
3-(3′,4′-diethoxybenzoyl)-2-[4′-(2-diethylaminoethoxy)phenyl]benzofuran
2-[4′-(2-diethylaminoethoxy)phenyl]-3-(3′-n-propoxybenzoyl)benzofuran
3-(4′-n-butoxybenzoyl)-2-[4′-(2-diethylaminoethoxy)phenyl]benzofuran
3-(3′,5′-t-butoxybenzoyl)-2-[4′-(2-diethylaminoethoxy)phenyl]benzofuran
2-[4′-(2-diethylaminoethoxy)phenyl]-3-(3′,4′,5′-trimethoxybenzoyl)benzofuran
2-[4′-(2-diethylaminoethoxy)phenyl]-3-(2′,5′-dimethoxy-4′-methylbenzoyl)benzofuran.

EXAMPLE 24

When 2-[4′-(2-bromoethoxy)phenyl]-3-(3′,5′-dimethoxybenzoyl)benzofuran is reacted with N-methylethylamine or N-methylpropylamine by the procedure described in Example 11, 3-(3′,5′-dimethoxybenzoyl)-2-[4′-(2-N-methylethylaminoethoxy)phenyl]benzofuran and 3-(3′,5′-dimethoxybenzoyl)-2-[4′-(2-N-methylpropylaminoethoxy)phenyl]benzofuran are prepared, respectively.

EXAMPLE 25

3-Benzoyl-2-[4′-(2-hydroxy-3-isopropylaminopropoxy)phenyl]benzofuran

To a mixture of 1.6 g. (0.04 mol.) of sodium hydroxide and 3.7 g. (0.012 mol.) of 3-benzoyl-2-p-hydroxyphenylbenzofuran was added with stirring 10.2 g. (0.11 mol.) of epichlorohydrin. The reaction mixture was refluxed for 1.5 hours, then it was cooled and extracted with methylene chloride. The extract was dried (MgSO$_4$) and concentrated to give a residue which, after chromatography, gave 3-benzoyl-2-[4′-(2,3-epoxypropoxy)phenyl]benzofuran.

3-Benzoyl-2-[4′-(2,3-epoxypropoxy)phenyl]benzofuran (1.9 g., 5.2 mmol.) was dissolved in 30 ml. of freshly distilled isopropylamine and the mixture was heated in a stainless steel pressure bomb at 100° for 4.5 hours. The contents of the bomb were concentrated under reduced pressure to give the title compound. The title compound was dissolved in ether and an ethereal solution of hydrochloric acid was added to precipitate the corresponding hydrochloride salt, m.p. 53°–59°.

EXAMPLE 26

2-[4′-(2-Hydroxy-3-isopropylaminopropoxy)phenyl]-3-(4′-methylbenzoyl)benzofuran

A mixture of 2.0 g. (6.1 mmol.) of 2-p-hydroxyphenyl-3-p-methylbenzoylbenzofuran, 2.6 g. (0.019 mol.) of epibromohydrin and 3.0 g. (0.021 mol.) of potassium carbonate in 100 ml. of dry acetone was refluxed for 12 hours. After cooling, the reaction mixture was filtered and the filtrate was concentrated to give 2-[4′-(2,3-epoxypropoxy)phenyl]-3-(4′-methylbenzoyl)benzofuran.

Substitution of an equivalent amount of 2-[4′-(2,3-epoxypropoxy)phenyl]-3-(4′-methylbenzoyl)benzofuran in the procedure of Example 25 for 3-benzoyl-2-(4′-(2,3-epoxypropoxy)phenyl]benzofuran gave the title compound. The title compound was converted to the corresponding hydrochloric acid salt as described in the previous example, m.p. 65°–75°.

EXAMPLE 27

3-(4'-Chlorobenzoyl)-2-[4'-(2-hydroxy-3isopropylaminopropoxy)phenyl]benzofuran

When an equivalent amount of 3-p-chlorobenzoyl-2-p-hydroxyphenylbenzofuran was reacted with epibromohydrin as described in the procedure of Example 26 and the product 3-(4'-chlorobenzoyl)-2-[4'-(2,3-epoxypropoxy)phenyl]benzofuran thus formed was treated with isopropylamine as described in the procedure of Example 25, the title compound was obtained.

The title compound was converted to the corresponding hydrochloride salt by treatment with an ethereal solution of hydrochloric acid as previously described, m.p. 177°–183°.

EXAMPLE 28

3-(3'-Chlorobenzoyl)-2-[4'-(2-hydroxy-3-isopropylaminopropoxy)phenyl]benzofuran

Treatment of 3-m-chlorobenzoyl-2-p-hydroxyphenylbenzofuran with epibromohydrin as described in Example 26 followed by reaction of the 3-(3'-chlorobenzoyl)-2-[4'-(2,3-epoxypropoxy)phenyl]benzofuran with isopropylamine as described in Example 25 gave the title compound.

Addition of ethereal hydrochloric acid solution to a solution of the title compound in ether gave the corresponding hydrochloric acid salt, m.p. 167°–172°.

EXAMPLE 29

3-(4'-Chlorobenzoyl)-2-[3'-(2-hydroxy-3-isopropylaminopropoxy)phenyl]benzofuran

When 2-m-methoxyphenylbenzofuran was acylated with p-chlorobenzoyl chloride and the product was demethylated with pyridine hydrochloride according to the procedure described in Example 1, 3-p-chlorobenzoyl-2-m-hydroxyphenylbenzofuran was obtained.

Substitution of an equivalent amount of 3-p-chlorobenzoyl-2-m-hydroxyphenylbenzofuran in the procedure of Example 26 in place of 2-p-hydroxyphenyl-3-p-methylbenzoylbenzofuran with subsequent opening of the epoxy compound thus formed with isopropylamine as previously described gave the title compound.

The title compound was converted to the corresponding hydrochloride salt as described hereinabove, m.p. 53°–60°.

EXAMPLE 30

2-[4'-(2-Hydroxy-3isopropylaminopropoxy)phenyl]-3-(3',5'-dimethylbenzoyl)benzofuran When an equivalent amount of 2-p-hydroxyphenyl-3-(3',5'-dimethylbenzoyl)benzofuran was substituted in the procedure of Example 26 for 2-p-hydroxyphenyl-3-p-methylbenzoylbenzofuran and the epoxy compound thus formed was opened with isopropylamine as previously described, the title compound was obtained.

The title compound was converted to the corresponding hydrochloride salt as described hereinabove, m.p. 154°–157°.

EXAMPLE 31

2-[4'-(2-Dimethylaminoethoxy)phenyl]-3-(3',4',5'-trimethylbenzoyl)benzofuran 2-p-Hydroxyphenyl-3-(3',4',5'-trimethylbenzoyl)-benzofuran (5.4 g., 15.3 mmol.) was dissolved in 200 ml. of dry acetone and 10.5 g. (0.076 mol.) of potassium carbonate and 2.10 g. (15.3 mmol.) of 2-dimethylaminoethyl chloride were added. The reaction mixture was refluxed for three hours, then it was cooled and filtered. The filtrate was concentrated under reduced pressure to give the title compound.

The title compound was dissolved in dry ether to which solution was added an ether solution of hydrochloric acid to give the corresponding hydrochloric acid salt, m.p. 197°–198°.

EXAMPLE 32

2-[4'-(3-Dimethylaminopropoxy)phenyl]-3-(3',5'-dimethylbenzoyl)benzofuran

Treatment of 2-p-hydroxyphenyl-3-(3',5'-dimethylphenyl)benzofuran with potassium carbonate and 3-dimethylaminopropyl chloride in dry acetone by the procedure described in Example 31 gave the title compound.

The title compound was converted to the corresponding hydrochloric acid salt as described hereinabove, m.p. 103°–106°.

EXAMPLE 33

2-Benzoyl-3-[4'-(3-diethylaminopropoxy)phenyl]benzofuran

Acylation of 3-p-methoxyphenylbenzofuran with benzoyl chloride and stannic chloride in methylene chloride as described in Example 1 for the preparation of 2-p-methoxyphenyl-3-p-methylbenzoylbenzofuran gives 2-benzoyl-3-p-methoxyphenylbenzofuran.

2-Benzoyl-3-p-methoxyphenylbenzofuran is demethylated with pyridine hydrochloride as previously described to give 2-benzoyl-3-p-hydroxyphenylbenzofuran, which upon reaction with 3-diethylaminopropyl chloride as described in Example 1, gives the title compound.

EXAMPLE 34

3-[4'-(2-Diethylaminoethoxy)phenyl]-2-(3',5'-dimethylbenzoyl)benzofuran

When 3-p-methoxyphenylbenzofuran is acylated with 3,5-dimethylbenzoyl chloride as described in the procedure of Example 1, 3-p-methoxyphenyl-2-(3',5'-dimethylbenzoyl)benzofuran is obtained.

Demethylation of 3-p-methoxyphenyl-2-(3',5'-dimethylbenzoyl)benzofuran followed by reaction of the 3-p-hydroxyphenyl-2-(3',5'-dimethylbenzoyl)benzofuran thus formed with 2-diethylaminoethyl chloride as described in Example 1 gives the title compound.

EXAMPLE 35

2-Benzoyl-3-[4'-(2-hydroxy-3-isopropylaminopropoxy)phenyl]benzofuran

Substitution of an equivalent amount of 2-benzoyl-3-p-hydroxyphenylbenzofuran in the procedure of Example 26 for 2-p-hydroxyphenyl-3-p-methylbenzoylbenzofuran with subsequent opening of the epoxy compound thus obtained with isopropylamine as described hereinabove gives the title compound.

EXAMPLE 36

3-[4'-(2-Diethylaminoethoxy)benzyl]-2-(3',5'-dimethylbenzoyl)benzofuran

To a solution of the Grignard reagent prepared from 4.27 g. (0.14 g.-atom) of magnesium turnings and 31.0 g. (0.13 mol.) of 4-iodoanisole in 50 ml. of ether was added dropwise a solution of 10.0 g. (0.07 mol.) of 3-cyanobenzofuran in 150 ml. of ether. The reaction mixture was stirred at 25° for 17 hours, then 30 ml. of water was added followed by a mixture of 20 ml. of sulfuric acid and 40 ml. of water. Additional amounts of the acid solution were added to dissolve the precipitate that formed in the reaction mixture. The mixture was poured into 500 ml. of water and the aqueous solution was extracted with chloroform. The extracts were dried (MgSO$_4$) and concentrated in vacuo to give 3-(4'-methoxybenzoyl)benzofuran which was purified by chromatography on alumina with chloroform, m.p. 89°–90° (hexane-benzene).

Hydrazine hydrate (28.0 g., 0.5 mol.) is added to a solution of 40.4 g. (0.16 mol.) of 3-(4'-methoxybenzoyl)benzofuran in 400 ml. of ethanol and the reaction mixture is refluxed overnight. The solution is concentrated in vacuo, chloroform is added and the chloroform solution is washed with saturated aqueous sodium chloride, dried (MgSO$_4$) and concentrated to yield the corresponding hydrazone. The hydrazone is dissolved in 100 ml. of dry dimethyl sulfoxide and added dropwise over a four hour interval to a slurry of 36.4 g. (0.32 mol.) of potassium t-butoxide in 100 ml. of dry dimethyl sulfoxide. The reaction mixture is poured into 500 ml. of water and the aqueous solution is extracted with chloroform. The extracts are washed with water, dried (MgSO$_4$) and concentrated to give 3-p-methoxybenzylbenzofuran.

Acylation of 3-p-methoxybenzylbenzofuran with 3,5-dimethylbenzoyl chloride and stannic chloride in methylene chloride according to the procedure described in Example 1 gives 3-p-methoxybenzyl-2-(3',5'-dimethylbenzoyl)benzofuran.

Demethylation of 3-p-methoxybenzyl-2-(3',5'-dimethylbenzoyl)benzofuran with pyridine hydrochloride as described above followed by reaction of the 3-p-hydroxybenzyl-2-(3',5'-dimethylbenzoyl)benzofuran thus obtained with 2-diethylaminoethyl chloride as described in Example 1 gives the title compound.

EXAMPLE 37

3-[4'-(2-Hydroxy-3-isopropylaminopropoxy)benzyl]-2-(3',5'-dimethylbenzoyl)benzofuran Substitution of an equivalent amount of 3-p-hydroxybenzyl-2-(3',5'-dimethylbenzoyl)benzofuran in the procedure of Example 26 for 2-p-hydroxyphenyl-3-p-methylbenzoylbenzofuran with subsequent opening of the epoxy compound thus obtained with isopropylamine as described hereinabove gives the title compound.

EXAMPLE 38

2-[4'-(2-Diethylaminoethoxy)phenyl]-5-methoxy-3-(3',5'-dimethylbenzoyl)benzofuran A mixture of 27.7 g. (0.1 mol.) of α-bromo-p-(2-chloroethoxy)acetophenone, 12.4 g. (0.1 mol.) of p-methoxyphenol and 13.8 g. (0.1 mol.) of potassium carbonate in 75 ml. of dry acetone is refluxed with stirring for 16 hours. After cooling, the reaction mixture is poured into 500 ml. of water. The product is collected and dissolved in chloroform and the chloroform solution is washed with water, dried (MgSO$_4$) and concentrated to give p-(2-chloroethoxy)-α-(p-methoxyphenoxy)acetophenone.

p-(2-Chloroethoxy)-α-(p-methoxyphenoxy)acetophenone (14.4 g., 0.045 mol.) is added to 90 g. of polyphosphoric acid preheated to 130° and the reaction mixture is vigorously stirred for 12 hours. The mixture is poured into 800 ml. of water and the aqueous phase is extracted three times with ether. The extracts are combined, washed with water, saturated aqueous sodium bicarbonate solution and saturated aqueous sodium chloride solution and dried (MgSO$_4$). Removal of the solvent gives 2-[4'-(2-chloroethoxy)phenyl]-5-methoxybenzofuran.

Acylation of 2-[4'-(2-chloroethoxy)phenyl]-5-methoxybenzofuran with 3,5-dimethylbenzoyl chloride as described in the procedure of Example 11 gives 2-[4'-(2-chloroethoxy)phenyl]-5-methoxy-3-(3',5'-dimethylbenzoyl)benzofuran.

Reaction of 2-[4'-(2-chloroethoxy)phenyl]-5-methoxy-3-(3',5'-dimethylbenzoyl)benzofuran with diethylamine by the procedure of Example 25 gives the title compound.

EXAMPLE 39

When an equivalent amount of a phenol listed below:
4-bromophenol
4-n-butoxyphenol
4-t-butylphenol
4-nitrophenol
α,α,α-trifluoro-p-cresol
is substituted in the procedure of Example 38 for p-methoxyphenol and the resulting p-(2-chloroethoxy)-α-substituted phenoxyacetophenone is reacted with polyphosphoric acid as described therein, there are obtained the following 2-[4'-(2-chloroethoxy)phenyl]-5-substituted benzofurans:

2-[4'-(2-chloroethoxy)phenyl]-5-bromobenzofuran
2-[4'-(2-chloroethoxy)phenyl]-5-n-butoxybenzofuran
2-[4'-(2-chloroethoxy)phenyl]-5-t-butylbenzofuran
2-[4'-(2-chloroethoxy)phenyl]-5-nitrobenzofuran
2-[4'-(2-chloroethoxy)phenyl]-5-trifluoromethylbenzofuran.

Acylation of a 5-substituted benzofuran listed above with 3,5-dimethylbenzoyl chloride as described in the procedure of Example 11 followed by treatment of the acylated benzofuran product thus obtained with diethylamine by the procedure of Example 25 gives the following compounds of this invention:

5-bromo-2-[4'-(2-diethylaminoethoxy)phenyl]-3-(3',5'-dimethylbenzoyl)benzofuran
5-n-butoxy-2-[4'-(2-diethylaminoethoxy)phenyl]-3-(3',5'-dimethylbenzoyl)benzofuran
5-n-butyl-2-[4'-(2-diethylaminoethoxy)phenyl]-3-(3',5'-dimethylbenzoyl)benzofuran
2-[4'-(2-diethylaminoethoxy)phenyl]-3-(3',5'-dimethylbenzoyl)-5-nitrobenzofuran
2-[4'-(2-diethylaminoethoxy)phenyl]-3-(3',5'-dimethylbenzoyl)-5-trifluoromethylbenzofuran.

EXAMPLE 40

Substitution of an equivalent amount of 2-m-hydroxyphenyl-3-(3',5'-dimethylbenzoyl)benzofuran in the procedure of Example 26 for 2-p-hydroxyphenyl-3-p-methylbenzoylbenzofuran followed by opening of the epoxy compound thus formed with isopropylamine as described in Example 25 gives 2-[3'-(2-hydroxy-3-isopropylaminopropoxy)phenyl]-3-(3',5'-dimethylbenzoyl)benzofuran.

In a similar manner, 2-[2'-(2-hydroxy-3-isopropylaminopropoxy)phenyl]-3-(4'-methylbenzoyl)benzofuran is prepared when 2-o-hydroxyphenyl-3-(4'- methylbenzoyl)benzofuran is used as the starting material.

EXAMPLE 41

2-(4'-Chlorobenzoyl)-3-[4'-(2-hydroxy-3-isopropylaminopropoxy)phenyl]benzofuran

When 3-p-methoxyphenylbenzofuran was acylated with p-chlorobenzoyl chloride as described in the procedure of Example 1, 2-p-chlorobenzoyl-3-p-methoxyphenylbenzofuran was obtained.

Demethylation of 2-p-chlorobenzoyl-3-p-methoxyphenylbenzofuran as previously described followed by substitution of the 2-p-chlorobenzoyl-3-p-hydroxyphenylbenzofuran thus formed in the procedure of Example 26 for 2-p-hydroxyphenyl-3-p-methylbenzoylbenzofuran with subsequent opening of the epoxy compound thus obtained with isopropylamine as described hereinabove gave the title compound, which was converted to the corresponding hydrochloride salt by the procedure described in Example 1, m.p. 198°–202°.

EXAMPLE 42

3-(3',5'-Dimethylbenzoyl)-2-[4'-(2-N-piperidinoethoxy)phenyl]benzofuran

A. Reaction of 2-[4'-(2-bromoethoxy)phenyl]-3-(3',5'-dimethylbenzoyl)benzofuran with piperidine as described in Example 11 gave the title compound.

The title compound was converted to the corresponding hydrochloride salt by the procedure of Example 1, m.p. 192°–194°.

B. An aqueous solution of 2-N-piperidinoethyl chloride hydrochloride was made basic by addition of aqueous sodium hydroxide solution. The solution was extracted with ether and the extract was dried (MgSO₄) and concentrated to give 2-N-piperidinoethyl chloride.

3-(3',5'-Dimethylbenzoyl)-2-p-hydroxyphenylbenzofuran (1.2 g., 35 mmol.) was dissolved in 50 ml. of 3-pentanone and 2 g. of potassium carbonate and a little potassium iodide were added. 2-N-piperidinoethyl chloride (0.6 g., 4 mmol.) was added and the reaction mixture was refluxed for 12 hours. The mixture was filtered and the filtrate concentrated in vacuo to give the title compound as an oil which was dissolved in ether and converted to the corresponding hydrochloride salt by addition of an ethereal solution of hydrochloric acid.

EXAMPLE 43

3-(3',5'-Dimethylbenzoyl)-2-[4'-(3-N-piperidinopropoxy)phenyl]benzofuran

A mixture of 3.0 g. of 3-(3',5'-dimethylbenzoyl)-2-p-hydroxyphenylbenzofuran, 5 g. of potassium carbonate and 25 ml. of 1,3-dibromopropane in 100 ml. of 3-pentanone was heated at 100° for 12 hours. The reaction mixture was filtered and the filtrate was evaporated. The residue was dissolved in hot ethanol from which solution precipitated 2-[4'-(3-bromopropoxy)phenyl]-3-(3',5'-dimethylbenzoyl)benzofuran, m.p. 102°–104°.

Substitution of 2-[4'-(3-bromopropoxy)phenyl]-3-(3',5'-dimethylbenzoyl)benzofuran in procedure A of Example 42 in place of 2-[4'-(2-bromoethoxy)phenyl]-3-(3',5'-dimethylbenzoyl)benzofuran gave the title compound.

The title compound was converted to the corresponding hydrochloride salt by the procedure of Example 1, m.p. 188°–190°.

EXAMPLE 44

3-(3',5'-Dimethylbenzoyl)-2-[4'-(2-N-morpholinoethoxy)phenyl]benzofuran

Use of morpholine in place of piperidine in procedure A of Example 42 gave the title compound.

The title compound was converted to the corresponding hydrochloride salt by the procedure of Example 1, m.p. 171°–173°.

EXAMPLE 45

3-(3',5'-Dimethylbenzoyl)-2-(4'-[2-N-(4-methylpiperazino)ethoxy]phenyl)benzofuran Substitution of N-methylpiperazine for piperidine in procedure A of Example 42 gave the title compound.

The title compound was converted to the corresponding hydrochloride salt by the procedure of Example 1, m.p. 175°–178°.

Similarly, 3-(3',5'-dimethylbenzoyl)-2-(4'-[2-N-(4-ethyl-, 4-propyl- and 4-butylpiperazino)ethoxy]phenyl)benzofuran are prepared by use of the corresponding N-(lower alkyl)-piperazine in place of N-methylpiperazine.

EXAMPLE 46

3-(3',5'-Dimethylbenzoyl)-2-[4'-(2-N-pyrrolidinoethoxy)phenyl]benzofuran

Use of pyrrolidine in procedure A of Example 42 in place of piperidine gave the title compound.

The title compound was converted to the corresponding hydrochloride salt by the procedure of Example 1, m.p. 160°–163°.

EXAMPLE 47

3-(3',5'-Dimethylbenzoyl)-2-[4'-(2-N-perhydroazepinoethoxy)phenyl]benzofuran

Substitution of perhydroazepine in procedure A of Example 42 for piperidine gave the title compound.

The title compound was converted to the corresponding hydrochloride salt by the procedure of Example 1, m.p. 174°–177°.

EXAMPLE 48

Acylation of a 5-substituted benzofuran listed below, prepared as described hereinabove:
2-[4'-(2-chloroethoxy)phenyl]-5-methoxybenzofuran
2-[4'-(2-chloroethoxy)phenyl]-5-bromobenzofuran
2-[4'-(2-chloroethoxy)phenyl]-5-n-butoxybenzofuran
2-[4'-(2-chloroethoxy)phenyl]-5-t-butylbenzofuran
2-[4'-(2-chloroethoxy)phenyl]-5-nitrobenzofuran
2-[4'-(2-chloroethoxy)phenyl]-5-trifluoromethylbenzofuran with 3,5-dimethylbenzoyl chloride as described in the procedure of Example 11 followed by treatment of the acylated benzofuran product thus obtained with piperidine by procedure A of Example 42 gives the following compounds of this invention, respectively:
3-(3',5'-dimethylbenzoyl)-5-methoxy-2-[4'-(2-N-piperidinoethoxy)phenyl]benzofuran
5-bromo-3-(3',5'-dimethylbenzoyl)-2-[4'-(2-N-piperidinoethoxy)phenyl]benzofuran
5-n-butoxy-3-(3',5'-dimethylbenzoyl)-2-[4'-(2-N-piperidinoethoxy)phenyl]benzofuran 5-t-butyl-3-(3',5'-dimethylbenzoyl)-2-[4'-(2-N-piperidinoethoxy)phenyl] benzofuran 3-(3',5'-dimethylbenzoyl)-5-nitro-2-[4'-(2-N-piperidinoethoxy)phenyl]benzofuran 3-(3',5'-dimethylbenzoyl)-2-[4'-(2-N-piperidinoethoxy)phenyl]-5-trifluoromethylbenzofuran.

EXAMPLE 49

When a substituted benzofuran listed below:
5-chloro-3-(3',5'-dimethylbenzoyl)-2-p-hydroxyphenylbenzofuran
4-chloro-3-(3',5'-dimethylbenzoyl)-2-p-hydroxyphenylbenzofuran
6-chloro-3-(3',5'-dimethylbenzoyl)-2-p-hydroxyphenylbenzofuran
7-ethyl-3-(3',5'-dimethylbenzoyl)-2-p-hydroxyphenylbenzofuran
5-fluoro-3-(3',5'-dimethylbenzoyl)-2-p-hydroxyphenylbenzofuran
5-methyl-3-(3',5'-dimethylbenzoyl)-2-p-hydroxyphenylbenzofuran is used in procedure B of Example 42 in place of 3-(3',5'-dimethylbenzoyl)-2-p-hydroxyphenylbenzofuran, the following compounds of this invention are obtained, respectively:
5-chloro-3-(3',5'-dimethylbenzoyl)-2-[4'-(2-N-piperidinoethoxy)phenyl]benzofuran
4-chloro-3-(3',5'-dimethylbenzoyl)-2-[4'-(2-N-piperidinoethoxy)phenyl]benzofuran
6-chloro-3-(3',5'-dimethylbenzoyl)-2-[4'-(2-N-piperidinoethoxy)phenyl]benzofuran
3-(3',5'-dimethylbenzoyl)-7-ethyl-2-[4'-(2-N-piperidinoethoxy)phenyl]benzofuran
3-(3',5'-dimethylbenzoyl)-5-fluoro-2-[4'-(2-N-piperidinoethoxy)phenyl]benzofuran
3-(3',5'-dimethylbenzoyl)-5-methyl-2-[4'-(2-N-piperidinoethoxy)phenyl]benzofuran.

EXAMPLE 50

Reaction of a hydroxyphenyl benzofuran listed below, prepared as described hereabove;
2-p-hydroxyphenyl-3-p-methylbenzoylbenzofuran
3-benzoyl-2-p-hydroxyphenylbenzofuran
3-p-chlorobenzoyl-2-p-hydroxyphenylbenzofuran
3-(3',5'-dichlorobenzoyl)-2-p-hydroxyphenylbenzofuran
2-p-hydroxyphenyl-3-(3',4',5'-trimethylbenzoyl)benzofuran
3-p-bromobenzoyl-2-p-hydroxyphenylbenzofuran
3-m-fluorobenzoyl-2-p-hydroxyphenylbenzofuran
3-(3',5'-dibromobenzoyl)-2-p-hydroxyphenylbenzofuran
3-(2',3'-difluorobenzoyl)-2-p-hydroxyphenylbenzofuran
3-(2',3',5'-trichlorobenzoyl)-2-p-hydroxyphenylbenzofuran
2-(2'-hydroxybenzyl)-3-(4'-methylbenzoyl)benzofuran
3-(3',5'-diethylbenzoyl)-2-hydroxyphenylbenzofuran
2-p-hydroxyphenyl-3-(4'-n-propylbenzoyl)benzofuran
3-(4'-t-butylbenzoyl)-2-p-hydroxyphenylbenzofuran
3-(3',5'-di-t-butylbenzoyl)-2-p-hydroxyphenylbenzofuran
with 2-N-piperidinoethyl chloride by procedure B of Example 42 gives the following compounds of this invention, respectively:

3-(4'-methylbenzoyl)-2-[4'-(2-N-piperidinoethoxy)phenyl]benzofuran
3-benzoyl-2-[4'-(2-N-piperidinoethoxy)phenyl]benzofuran
3-(4'-chlorobenzoyl)-2-[4'-(2-N-piperidinoethoxy)phenyl]benzofuran
3-(3',5'-dichlorobenzoyl)-2-[4'-(2-N-piperidinoethoxy)phenyl]benzofuran
2-[4'-(2-N-piperidinoethoxy)phenyl]-3-(3',4',5'-trimethylbenzoyl)benzofuran
3-(4'-bromobenzoyl)-2-[4'-(2-N-piperidinoethoxy)phenyl]benzofuran
3-(3'-fluorobenzoyl)-2-[4'-(2-N-piperidinoethoxy)phenyl]benzofuran
3-(3',5'-dibromobenzoyl)-2-[4'-(2-N-piperidinoethoxy)phenyl]benzofuran
3-(2',3'-difluorobenzoyl)-2-[4'-(2-N-piperidinoethoxy)phenyl]benzofuran
2-[4'-(2-N-piperidinoethoxy)phenyl]-3-(2',3',5'-trichlorobenzoyl)benzofuran
3-(4'-methylbenzoyl)-2-[2'-(2-N-piperidinoethoxy)phenyl]benzofuran
3-(3',5'-diethylbenzoyl)-2-[4'-(2-N-piperidinoethoxy)phenyl]benzofuran
2-[4'-(2-N-piperidinoethoxy)phenyl]-3-(4'-n-propylbenzoyl)benzofuran
3-(4'-t-butylbenzoyl)-2-[4'-(2-N-piperidinoethoxy)phenyl]benzofuran
3-(3',5'-di-t-butylbenzoyl)-2-[4'-(2-N-piperidinoethoxy)phenyl]benzofuran.

EXAMPLE 51

3-p-Anisoyl-2-[4'-(2-N-piperidinoethoxy)phenyl]benzofuran

When p-anisoyl chloride and 2-[4'-(2-bromoethoxy)phenyl]benzofuran are reacted by the procedure described in Example 11 and the 2-[4'-(2-bromoethoxy)phenyl]-3-p-anisoylbenzofuran thus obtained is treated with piperidine as described in Example 11, the title compound is obtained.

EXAMPLE 52

Reaction of a benzofuran listed below, prepared as in Examples 11, 12 and 23:
2-[4'-(2-bromoethoxy)phenyl]-3-(3',5'-dimethoxybenzoyl)benzofuran
2-[4'-(2-bromoethoxy)phenyl]-3-(3',5'-dimethyl-4'-methoxybenzoyl)benzofuran
2-[4'-(2-bromoethoxy)phenyl]-3-(3',4'-diethoxybenzoyl)benzofuran
2-[4'-(2-bromoethoxy)phenyl]-3-(3'-n-propoxybenzoyl)benzofuran
2-[4'-(2-bromoethoxy)phenyl]-3-(4'-n-butoxybenzoyl)benzofuran
2-[4'-(2-bromoethoxy)phenyl]-3-(3',5'-di-t-butoxybenzoyl)benzofuran
2-[4'-(2-bromoethoxy)phenyl]-3-(3',4',5'-trimethoxybenzoyl)benzofuran
2-[4'-(2-bromoethoxy)phenyl]-3-(2',5'-dimethoxy-4'-methylbenzoyl)benzofuran with piperidine as described in the procedure of Example 11 gives the following compounds, respectively:
3-(3',5'-dimethoxybenzoyl)-2-[4'-(2-N-piperidinoethoxy)phenyl]benzofuran
3-(3',5'-dimethyl-4'-methoxybenzoyl)-2-[4'-(2-N-piperidinoethoxy)phenyl]benzofuran 3-(3',4'-diethoxybenzoyl)-2-[4'-(2-N-piperidinoethoxy)phenyl]benzofuran 2-[4'-(2-N-piperidinoethoxy)phenyl]-3-(3'-n-propoxybenzoyl)benzofuran 3-(4'-n-butoxybenzoyl)-2-[4'-(2-N-piperidinoethoxy)phenyl]benzofuran 3-(3',5'-di-t-butoxybenzoyl)-2-[4'-(2-N-piperidinoethoxy)phenyl]benzofuran 2-[4'-(2-N-piperidinoethoxy)phenyl]-3-(3',4',5'-trimethoxybenzoyl)benzofuran 3-(2',5'-dimethoxy-4'-methylbenzoyl)-2-[4'-(2-N-piperidinoethoxy(phenyl[benzofuran.

EXAMPLE 53

Reaction of the following hydroxyphenyl benzofurans prepared hereinabove:

2-benzoyl-3-p-hydroxyphenylbenzofuran 3-p-hydroxyphenyl-2-(3',5'-dimethylbenzoyl)benzofuran 3-p-hydroxybenzyl-2-(3',5'-dimethylbenzoyl)benzofuran with 2-N-piperidinoethyl chloride as described in procedure B of Example 42 gives the compounds of this invention listed below:

2-benzoyl-3-[4'-(2-N-piperidinoethoxy)phenyl]benzofuran 2-(3',5'-dimethylbenzoyl)-3-[4'-(2-N-piperidinoethoxy)phenyl]benzofuran 2-(3',5'-dimethylbenzoyl)-3-[4'-(2-N-piperidinoethoxy)benzyl]benzofuran.

EXAMPLE 54

Opening of the epoxide function of the substituted benzofurans listed below:

3-benzoyl-2-[4'-(2,3-epoxypropoxy)phenyl]benzofuran

2-[4'-(2,3-epoxypropoxy)phenyl]-3-(4'-methylbenzoyl)benzofuran 3-(4'-chlorobenzoyl)-2-[4'-(2,3-epoxypropoxy)phenyl]benzofuran 3-(3'-chlorobenzoyl)-2-[4'-(2,3-epoxypropoxy)phenyl]benzofuran 3-(4'-chlorobenzoyl)-2-[3'-(2,3-epoxypropoxy)phenyl]benzofuran 2-[4'-(2,3-epoxypropoxy)phenyl]-3-(3',5'-dimethylbenzoyl)benzofuran 2-benzoyl-3-[4'-(2,3-epoxypropoxy)phenyl]benzofuran 3-[4'-(2,3-epoxypropoxy)benzyl]-2-(3',5'-dimethylbenzoyl)benzofuran with piperidine according to the procedure described in Example 25 gives the following compounds of this invention, respectively:

3-benzoyl-2-[4'-(2-hydroxy-3-N-piperidinopropoxy)phenyl]benzofuran

2-[4'-(2-hydroxy-3-N-piperidinopropoxy)phenyl]-3-(4'-methylbenzoyl)benzofuran 3-(4'-chlorobenzoyl)-2-[4'-(2-hydroxy-3-N-piperidinopropoxy)phenyl]benzofuran 3-(3'-chlorobenzoyl)-2-[4'-(2-hydroxy-3-N-piperidinopropoxy)phenyl]benzofuran 3-(4'-chlorobenzoyl)-2-[3'-(2-hydroxy-3-N-piperidinopropoxy)phenyl]benzofuran 3-(3',5'-dimethylbenzoyl-2-[4'-(2-hydroxy-3-N-piperidinopropoxy)phenyl]benzofuran 2-benzoyl-3-[4'-(2-hydroxy-3-N-piperidinopropoxy)phenyl]benzofuran 2-(3',5'-dimethylbenzoyl)-3-[4'-(2-hydroxy-3-N-piperidinopropoxy)benzyl]benzofuran.

EXAMPLE 55

By using morpholine, N-methylpiperazine, pyrrolidine or perhydroazepine in the procedures of Examples 48, 52 and 54 in place of piperidine, the corresponding 2-N-morpholinoethoxy, 2-N-(4-methylpiperazino)ethoxy, 2-N-pyrrolidinoethoxy, 2-N-perhydroazepinoethoxy, 2-hydroxy-3-N-morpholinopropoxy, 2-hydroxy-3-N-(4-methylpiperazino)-propoxy, 2-hydroxy-3-N-pyrrolidinopropoxy, and 2-hydroxy-3-N-perhydroazopinopropoxy benzofurans are respectively obtained.

EXAMPLE 56

Addition of an ethereal solution of oxalic acid to a solution of 2-[4'-(3-diethylaminopropoxy)phenyl]-3-(4'-methylbenzoyl)benzofuran in ether gives the oxalate salt.

The corresponding hydrochloride salt may be prepared from the oxalate salt by passage of a solution of 2-[4'-(3-diethylaminopropoxy)phenyl]-3-(4'-methylbenzoyl) benzofuran oxalate in ethanol through an Amberlite IRA-401 chloride ion exchange column.

In a similar manner, other acid addition salts may be prepared.

EXAMPLE 57

| Ingredients | Amounts |
|---|---|
| 2-[4'-(2-Diethylaminoethoxy)phenyl]-3-(3',5'-dimethylbenzoyl)benzofuran | 100 mg. |
| Calcium sulfate dihydrate | 150 mg. |
| Sucrose | 25 mg. |
| Starch | 15 mg. |
| Talc | 5 mg. |
| Stearic acid | 3 mg. |

The sucrose, calcium sulfate dihydrate and 2-[4'-(2-diethylaminoethoxy)phenyl]-3-(3',5'-dimethylbenzoyl)benzofuran are thoroughly mixed and granulated with 10% gelatin solution. The wet granules are screened, dried and then mixed with the starch, talc and stearic acid, screened and compressed into a tablet.

EXAMPLE 58

| Ingredients | Amounts |
|---|---|
| 2-[4'-(2-Diethylaminoethoxy)phenyl]-3-(3',5'-dimethylbenzoyl)benzofuran | 150 mg. |
| Magnesium stearate | 5 mg. |
| Lactose | 100 mg. |

The ingredients are mixed and filled into a hard gelatin capsule.

The ingredients are mixed and filled into a hard gelatin capsule.

Similarly, the other substituted benzofurans disclosed herein may be formulated into tablets and capsules by the procedures of Examples 57 and 58.

The compositions prepared as in Examples 57 and 58 are administered orally to a subject in need of coronary vasodilator activity within the dose ranges given hereabove.

EXAMPLE 59

2-[3'-(3-Diethylaminopropoxy)phenyl]-3-(3',5'-dimethylbenzoyl)benzofuran

Reaction of 2-m-hydroxyphenyl-3-(3',5'-dimethylbenzoyl)benzofuran with 3-diethylaminopropyl chloride as described in the procedure of Example 7 gave the title compound which was converted to the corresponding hydrochloride salt as described hereinabove, m.p. 114°–121°.

EXAMPLE 60

2-[4'-(2-Diethylaminoethoxy)phenyl]-3-(2',5'-dimethylbenzoyl)benzofuran 2,5-Dimethylbenzoyl chloride was prepared from reaction of 2,5-dimethylbenzoic acid and thionyl chloride as described in Example 8.

Substitution of an equivalent amount of 2,5-dimethylbenzoyl chloride in the procedure of Example 7 for 3,5-dimethylbenzoyl chloride followed by demethylation of 2-p-methoxyphenyl-3-(2',5'-dimethylbenzoyl)benzofuran and reaction of the product thus formed with 2-diethylaminoethyl chloride as described therein gave the title compound.

The title compound was converted to the corresponding hydrochloride salt as previously described, m.p. 150°–153°.

EXAMPLE 61

2-[4'-(3-Dimethylaminopropoxy)phenyl]-3-(3',5'-dimethylbenzoyl)benzofuran

Reaction of 2-p-hydroxyphenyl-3-(3',5'-dimethylbenzoyl)benzofuran with 3-dimethylaminopropyl chloride according to the procedure described in Example 7 gave the title compound.

The title compound was converted to the corresponding hydrochloric acid salt as described in Example 7, m.p. 145°–150° C.

EXAMPLE 62

3-(3',5'-Diethylbenzoyl)-2-[4'-(2-N-pyrrolidinoethoxy)phenyl]benzofuran

Acylation of 2-[4'-(2-bromoethoxy)phenyl]benzofuran with 3,5-diethylbenzoyl chloride as described hereinabove gave 2-[4'-(2-bromoethoxy)phenyl]-3-(3',5'-diethylbenzoyl)benzofuran.

Reaction of 2-[4'-(2-bromoethoxy)phenyl]-3-(3',5'-diethylbenzoyl)benzofuran with pyrrolidine as described in Example 11 gave the title compound.

The title compound was converted to the corresponding hydrochloride salt by the procedure of Example 1, m.p. 157°–159°.

EXAMPLE 63

2-[4'-(2-Diethylaminoethoxy)phenyl]-3-(3',5'-dimethylbenzoyl)benzothiophene

When 2-p-methoxyphenylbenzothiophene was acylated with 3,5-dimethylbenzoyl chloride as described in the procedure of Example 1, 3-(3',5'-dimethylbenzoyl)-2-(4'-methoxyphenyl)benzothiophene was obtained.

Demethylation of 3-(3',5'-dimethylbenzoyl)-2-(4'-methoxyphenyl)benzothiophene with pyridine hydrochloride as previously described followed by reaction of the 3-(3',5'-dimethylbenzoyl-2-(4'-hydroxyphenyl)benzothiophene thus formed with 2-diethylaminoethyl chloride, also as described above, gave the title compound, m.p. 138°–142°.

EXAMPLE 64

3-[4'-(2-Diethylaminoethoxy)phenyl]-2-(3',5'-dimethylbenzoyl)benzothiophene

A solution of 11.0 g. (0.1 mol.) of thiophenol and 22.9 g. (0.1 mol.) of α-bromo-p-methoxyacetophenone in 40 ml. of pyridine is refluxed for four hours. Water is added to the reaction mixture and the solution is extracted with methylene chloride. The extract is washed with water, dried and evaporated to dryness to give p-methoxy-α-phenylthioacetophenone.

p-Methoxy-α-phenylthioacetophenone (5.0 g., 0.02 mol.) is heated with 35 g. of polyphosphoric acid and 25 ml. of phosphoric acid at 90°–120° until the reaction is determined to be complete by thin layer chromatography. The mixture is poured into ice-water and this mixture is extracted with ether. Evaporation of the solvent gives 3-p-methoxyphenylbenzothiophene.

3-p-Methoxyphenylbenzothiophene is acylated with 3,5-dimethylbenzoyl chloride as previously described to give 2-(3',5'-dimethylbenzoyl)-3-p-methoxyphenylbenzothiophene. Demethylation with pyridine hydrochloride followed by reaction of the hydroxy compound thus formed with diethylaminoethyl chloride as described above gives the title compound.

EXAMPLE 65

5-Chloro-2-[4'-(2-diethylaminoethoxy)phenyl]-3-(3',-5'-dimethylbenzoyl)benzothiophene When p-chlorothiophenol is substituted in the procedure of Example 38 for p-methoxyphenyl, p-(2-chloroethoxy)-α-(p-chlorophenylthio)acetophenone is obtained.

Cyclization of p-(2-chloroethoxy)-α-(p-chlorophenylthio)acetophenone with polyphosphoric acid as described in Example 38, followed by acylation of the product thus formed with 3,5-dimethylbenzoyl chloride as described in the procedure of Example 11 gives 5-chloro-2-[4'-(2-chloroethoxy)phenyl]-3-(3',5'-dimethylbenzoyl)benzothiophene.

Reaction of 5-chloro-2-[4'-(2-chloroethoxy)phenyl]-3-(3',5'-dimethylbenzoyl)benzothiophene with diethylamine by the procedure of Example 25 gives the title compound.

EXAMPLE 66

3-(3',5'-Dimethylbenzoyl)-2-[4'-(2-N-piperidinoethoxy)phenyl]benzothiophene

Reaction of 3-(3',5'-dimethylbenzoyl)-2-(4'-hydroxyphenyl)benzothiophene and 2-N-piperidinoethyl chloride according to the procedure described in Example 42-B gives the title compound.

EXAMPLE 67

| Ingredients | Amounts |
| --- | --- |
| 5-Chloro-2-[4'-(2-diethylaminoethoxy)phenyl]-3-(3',5'-dimethylbenzoyl)benzothiophene | 150 mg. |
| Magnesium stearate | 5 mg. |
| Lactose | 100 mg. |

The ingredients are mixed and filled into a hard gelatin capsule.

The ingredients are mixed and filled into a hard gelatin capsule.

What is claimed is:

1. A compound of the formula:

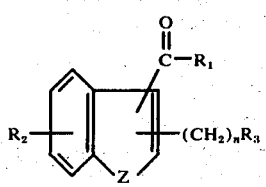

or a pharmaceutically acceptable acid addition salt thereof, in which:

$R_1$ is phenyl, halophenyl, dihalophenyl, trihalophenyl, lower alkylphenyl, di-lower alkylphenyl, tri-lower alkylphenyl, lower alkoxyphenyl, di-lower alkoxyphenyl, tri-lower alkoxyphenyl, lower alkyl-di-lower alkoxyphenyl or lower alkoxy-di-lower alkylphenyl;

$R_2$ is hydrogen, halo, lower alkyl, lower alkoxy, nitro or trifluoromethyl;

$R_3$ is 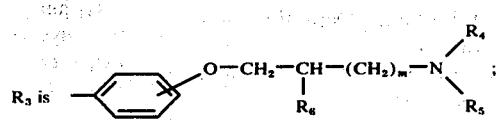

$R_4$ is hydrogen, methyl, ethyl or propyl and $R_5$ is methyl, ethyl or propyl or $R_4$ and $R_5$ together with the nitrogen atom to which they are attached form a pyrrolidine, piperidine, N-(lower alkyl)piperazine, morpholine or perhydroazepine ring;

$R_6$ is hydrogen or hydroxy;

m is 0 or 1 when $R_6$ is hydrogen and 1 when $R_6$ is hydroxy;

n is 0 or 1; and

Z is oxygen or sulfur.

2. A compound according to claim 1 in which Z is oxygen.

3. A compound according to claim 1 in which Z is sulphur.

4. A compound according to claim 2 in which $R_4$ is hydrogen, methyl, ethyl or propyl and $R_5$ is methyl, ethyl or propyl.

5. A compound according to claim 2 in which

is in the 3-position of the benzofuran nucleus; $R_1$ is dihalophenyl, trihalophenyl, di-lower alkylphenyl, tri-lower alkylphenyl, di-lower alkoxyphenyl, tri-lower alkoxyphenyl, lower alkyl-di-lower alkoxyphenyl or lower alkoxy-di-lower alkylphenyl; $R_2$ is hydrogen, halo or lower alkyl; —(CH$_2$)$_n$R$_3$ is in the 2-position of the benzofuran nucleus; $R_3$ is

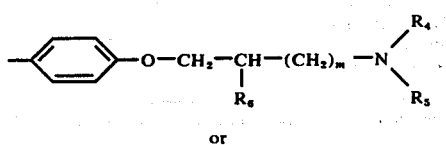

or

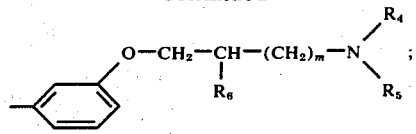

$R_4$ and $R_5$ are methyl, ethyl, propyl or together with the nitrogen atom to which they are attached form a pyrrolidine, piperidine, N-(lower alkyl)piperazine, morpholine or perhydroazepine ring and $R_6$ is hydrogen.

6. A compound according to claim 2 in which

is in the 3-position of the benzofuran nucleus; $R_1$ is halophenyl, 3,5-dihalophenyl, 3,5-di-lower alkylphenyl, 3,4,5-tri-lower alkylphenyl, 3,5-di-lower alkoxyphenyl or 3,5-di-lower alkyl-4-lower alkoxyphenyl; $R_2$ is hydrogen or halo; —(CH$_2$)$_n$R$_3$ is in the 2-position of the benzofuran nucleus; $R_3$ is

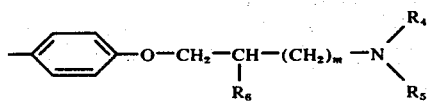

or

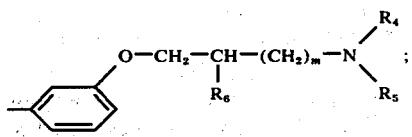

$R_4$ and $R_5$ are methyl, ethyl, propyl or together with the nitrogen atom to which they are attached form a pyrrolidine, piperidine, N-(lower alkyl)piperazine, morpholine or perhydroazepine ring and $R_6$ is hydrogen.

7. A compound according to claim 6 in which $R_1$ is chlorophenyl, 3,5-dimethylphenyl, 3,4,5-trimethylphenyl, 3,5-dimethoxyphenyl or 3,5-dimethyl-4-methoxyphenyl; $R_2$ is hydrogen or chloro; n is 0; $R_3$ is

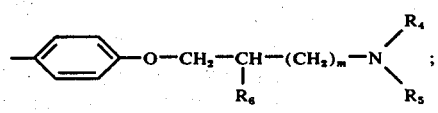

$R_4$ and $R_5$ are ethyl or together with the nitrogen atom to which they are attached form a pyrrolidine or piperidine ring and m is 0.

8. A compound according to claim 7 in which $R_4$ and $R_5$ are ethyl.

9. A compound according to claim 4 being the compound 2-(4'-chlorobenzoyl)-3-[4'-(2-hydroxy-3-isopropylaminopropoxy)phenyl]benzofuran.

10. A compound according to claim 7 being the compound 3-(3',5'-dimethylbenzoyl)-2-[4'-(2-pyrrolidinoethoxy)phenyl]benzofuran.

11. A compound according to claim 7 being the compound 3-(3',5'-dimethylbenzoyl)-2-[4'-(2-N-piperidinoethoxy)phenyl]benzofuran.

12. A compound according to claim 8 being the compound 2-[4'-(2-diethylaminoethoxy)phenyl]-3-(3',5'-dimethylbenzoyl)benzofuran.

13. A compound according to claim 8 being the compound 2-[4'-(2-diethylaminoethoxy)phenyl]-3-(3',4',5'-trimethylbenzoyl)benzofuran.

14. A compound according to claim 8 being the compound 5-chloro-2-[4'-(2-diethylaminoethoxy)phenyl]-3-(3',5'-dimethylbenzoyl)benzofuran.

15. A compound according to claim 8 being the compound 3-[4'-(2-diethylaminoethoxy)phenyl]-2-(3',5'-dimethylbenzoyl)benzofuran.

16. A compound according to claim 8 being the compound 2-[4'-(2-diethylaminoethoxy)phenyl]-3-(3',5'-diethylbenzoyl)benzofuran.

17. A compound according to claim 3 being the compound 2-[4'-(2-diethylaminoethoxy)phenyl]-3-(3',5'-dimethylbenzoyl)benzothiophene.

18. A compound according to claim 3 being the compound 5-chloro-2-[4'-(2-diethylaminoethoxy)phenyl]-3-(3',5'-dimethylbenzoyl)benzothiophene.

19. A compound according to claim 3 being the compound 3-[4'-(2-diethylaminoethoxy)phenyl]-2-(3',5'-dimethylbenzoyl)benzothiophene.

20. A pharmaceutical composition having coronary vasodilator activity comprising a pharmaceutical carrier and an effective and nontoxic amount of a compound of claim 1.

21. A method of producing coronary vasodilation comprising administering to an animal an effective and nontoxic amount of a compound of claim 1.

22. A pharmaceutical composition having anti-anginal activity comprising a pharmaceutical carrier and an effective and nontoxic amount of the compound 2-[4'-(2-diethylaminoethoxy)phenyl]-3-(3',5'-dimethylbenzoyl)benzofuran.

23. A method of producing anti-anginal activity comprising administering to an animal an effective and nontoxic amount of the compound 2-[4'-(2-diethylaminoethoxy)phenyl]-3-(3',5'-dimethylbenzoyl)benzofuran.

* * * * *